US010258505B2

(12) United States Patent
Ovchinnikov

(10) Patent No.: US 10,258,505 B2
(45) Date of Patent: Apr. 16, 2019

(54) BALANCED PHACOEMULSIFICATION TIP

(75) Inventor: Mikhail A. Ovchinnikov, Laguna Niguel, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 1498 days.

(21) Appl. No.: 12/884,285

(22) Filed: Sep. 17, 2010

(65) Prior Publication Data

US 2012/0072197 A1 Mar. 22, 2012

(51) Int. Cl.
*A61B 17/32* (2006.01)
*A61F 9/007* (2006.01)

(52) U.S. Cl.
CPC ............. *A61F 9/00745* (2013.01); *A61B 2017/320098* (2017.08)

(58) Field of Classification Search
CPC ............. A61F 9/00745; A61F 9/00736; A61B 2017/320072; A61B 2017/320096; A61B 2017/320068; A61B 17/320068; A61B 2017/320069; A61B 2017/32007; A61B 2017/320071; A61B 2017/320073; A61B 2017/320074; A61B 2017/320075; A61B 2017/320077; A61B 2017/32008; A61B 2017/320082; A61B 2017/320084; A61B 2017/320088; A61B 2017/320089; A61B 2017/320092; A61B 2017/320098
USPC ...................................... 606/169; 310/323.18
See application file for complete search history.

(56) References Cited

U.S. PATENT DOCUMENTS

| 312,408 | A | 2/1885 | Wackerhagen |
| 1,397,395 | A | 11/1921 | Bixler |
| 2,070,281 | A | 2/1937 | Leggiadro |
| 2,514,080 | A | 7/1950 | Mason |
| 2,651,148 | A | 9/1953 | Carwile |
| 2,774,193 | A | 12/1956 | Thatcher et al. |
| 2,874,470 | A | 2/1959 | Richards |

(Continued)

FOREIGN PATENT DOCUMENTS

| AU | 2003241752 | 9/2003 |
| AU | 2011202357 | 6/2011 |

(Continued)

OTHER PUBLICATIONS

International Searching Authority, International Search Report, International Application No. PCT/US2011/046362, dated Mar. 16, 2012, 4 pages.

(Continued)

*Primary Examiner* — Diane Yabut
*Assistant Examiner* — Martin T. Ton

(57) ABSTRACT

In various embodiments, a phacoemulsification tip may include a shaft and a cutting edge portion having at least a first and second bend. The geometry of the tip may be configured to result in a lateral displacement ($u_x$), perpendicular to the shaft during torsional vibration of the tip at frequencies between 10 kHz and 60 kHz, of less than approximately 5% to 25% (e.g., 15%) of the lateral displacement at the distal end point of the tip throughout a portion of the shaft extending from the end of a conical portion of the tip through to the first bend in the cutting edge portion of the tip. Software and/or physical modeling may be used to determine the tip geometry.

20 Claims, 14 Drawing Sheets

(56) References Cited

U.S. PATENT DOCUMENTS

| | | |
|---|---|---|
| 2,990,616 A | 7/1961 | Balamuth et al. |
| RE25,033 E | 8/1961 | Balamuth et al. |
| 3,053,124 A | 9/1962 | Balamuth et al. |
| 3,086,288 A | 4/1963 | Balamuth et al. |
| 3,133,351 A | 5/1964 | Von Seggern |
| 3,257,721 A | 6/1966 | Joens et al. |
| 3,433,226 A | 3/1969 | Boyd |
| 3,513,848 A | 5/1970 | Winston et al. |
| 3,518,766 A | 7/1970 | Burt |
| 3,526,219 A | 9/1970 | Balamuth |
| 3,546,498 A | 12/1970 | McMaster et al. |
| 3,565,062 A | 2/1971 | Kuris |
| 3,589,363 A | 6/1971 | Banko |
| 3,601,126 A | 8/1971 | Estes |
| 3,610,080 A | 10/1971 | Kuris |
| 3,657,056 A | 4/1972 | Winston et al. |
| 3,693,613 A | 9/1972 | Kelman |
| 3,703,037 A | 11/1972 | Robinson |
| 3,812,855 A | 5/1974 | Banko |
| 3,812,858 A | 5/1974 | Oringer |
| 3,830,240 A | 8/1974 | Antonevich et al. |
| 3,857,387 A | 12/1974 | Shock |
| 3,861,391 A | 1/1975 | Antonevich et al. |
| 3,888,004 A | 6/1975 | Coleman |
| 3,902,495 A | 9/1975 | Weiss et al. |
| 3,930,173 A | 12/1975 | Banko |
| 3,930,505 A | 1/1976 | Wallach |
| 3,937,990 A | 2/1976 | Winston |
| 3,942,519 A | 3/1976 | Shock |
| 3,943,932 A | 3/1976 | Woo |
| 3,952,732 A | 4/1976 | Shock |
| 3,956,826 A | 5/1976 | Perdreaux, Jr. |
| 3,964,487 A | 6/1976 | Judson |
| 3,990,452 A | 11/1976 | Murry et al. |
| 4,012,647 A | 3/1977 | Balamuth et al. |
| 4,024,467 A | 5/1977 | Andrews et al. |
| 4,024,866 A | 5/1977 | Wallach |
| 4,063,557 A | 12/1977 | Wuchinich et al. |
| 4,065,687 A | 12/1977 | Mishiro |
| 4,114,623 A | 9/1978 | Meinke et al. |
| 4,126,137 A | 11/1978 | Archibald |
| 4,136,700 A | 1/1979 | Broadwin et al. |
| 4,156,187 A | 5/1979 | Murry et al. |
| 4,168,707 A | 9/1979 | Douvas et al. |
| 4,169,984 A | 10/1979 | Parisi |
| 4,173,725 A | 11/1979 | Asai et al. |
| 4,184,510 A | 1/1980 | Murry et al. |
| 4,223,676 A | 9/1980 | Wuchinich et al. |
| 4,246,902 A | 1/1981 | Martinez |
| 4,248,232 A | 2/1981 | Engelbrecht et al. |
| 4,283,175 A | 8/1981 | Nash |
| 4,406,284 A | 9/1983 | Banko |
| 4,417,578 A | 11/1983 | Banko |
| 4,425,115 A | 1/1984 | Wuchinich |
| 4,493,694 A | 1/1985 | Wuchinich |
| 4,496,342 A | 1/1985 | Banko |
| 4,504,264 A | 3/1985 | Kelman |
| 4,508,532 A | 4/1985 | Drews et al. |
| 4,515,583 A | 5/1985 | Sorich |
| 4,526,571 A | 7/1985 | Wuchinich |
| 4,530,359 A | 7/1985 | Helfgott et al. |
| 4,561,438 A | 12/1985 | Bonnet et al. |
| 4,587,958 A | 5/1986 | Noguchi et al. |
| 4,589,415 A | 5/1986 | Haaga |
| 4,590,935 A | 5/1986 | Ranalli |
| 4,609,368 A | 9/1986 | Dotson, Jr. |
| 4,651,280 A | 3/1987 | Chang et al. |
| 4,658,819 A | 4/1987 | Harris et al. |
| 4,676,243 A | 6/1987 | Clayman |
| 4,697,117 A | 9/1987 | Mishiro |
| 4,705,500 A | 11/1987 | Reimels et al. |
| 4,705,980 A | 11/1987 | Mishiro |
| 4,706,669 A | 11/1987 | Schlegel |
| 4,712,544 A | 12/1987 | Ensslin |
| 4,739,759 A | 4/1988 | Rexroth et al. |
| 4,750,488 A | 6/1988 | Wuchnich et al. |
| 4,750,902 A | 6/1988 | Wuchnich et al. |
| 4,766,897 A | 8/1988 | Smirmaul |
| 4,770,654 A | 9/1988 | Rogers et al. |
| 4,793,346 A | 12/1988 | Mindich |
| 4,812,697 A | 3/1989 | Mishiro |
| 4,816,018 A | 3/1989 | Parisi |
| 4,827,911 A | 5/1989 | Broadwin et al. |
| 4,832,683 A | 5/1989 | Idemoto et al. |
| 4,869,715 A | 9/1989 | Sherburne |
| 4,869,716 A | 9/1989 | Smirmaul |
| 4,885,499 A | 12/1989 | Ueha et al. |
| 4,911,161 A | 3/1990 | Schecter |
| 4,920,954 A | 5/1990 | Alliger et al. |
| 4,922,902 A | 5/1990 | Wuchinich et al. |
| 4,950,272 A | 8/1990 | Smirmaul |
| 4,961,424 A | 10/1990 | Kubota et al. |
| 4,965,482 A | 10/1990 | Ohnishi et al. |
| 4,969,885 A | 11/1990 | Farin |
| 4,974,581 A | 12/1990 | Wiksell |
| 4,989,583 A | 2/1991 | Hood |
| 4,989,588 A | 2/1991 | Kubota et al. |
| 4,992,048 A | 2/1991 | Goof |
| 5,019,083 A | 5/1991 | Klapper et al. |
| 5,026,387 A | 6/1991 | Thomas |
| 5,047,008 A | 9/1991 | de Juan, Jr. et al. |
| 5,047,043 A | 9/1991 | Kubota et al. |
| 5,062,827 A | 11/1991 | Wiksell |
| 5,084,012 A | 1/1992 | Kelman |
| 5,094,617 A | 3/1992 | Carr |
| 5,112,300 A | 5/1992 | Ureche |
| 5,112,339 A | 5/1992 | Zelman |
| 5,116,343 A | 5/1992 | Ams et al. |
| 5,116,352 A | 5/1992 | Schnepp-Pesch et al. |
| 5,139,509 A | 8/1992 | Fischer et al. |
| 5,151,085 A | 9/1992 | Sakurai et al. |
| 5,154,694 A | 10/1992 | Kelman |
| 5,154,696 A | 10/1992 | Shearing |
| 5,160,317 A | 11/1992 | Costin |
| 5,176,677 A | 1/1993 | Wuchinich |
| 5,180,363 A | 1/1993 | Idemoto et al. |
| 5,188,102 A | 2/1993 | Idemoto et al. |
| 5,188,589 A | 2/1993 | Wypych et al. |
| 5,205,817 A | 4/1993 | Idemoto et al. |
| 5,213,569 A | 5/1993 | Davis |
| 5,217,465 A | 6/1993 | Steppe |
| 5,221,282 A | 6/1993 | Wuchinich |
| 5,222,937 A | 6/1993 | Kagawa |
| 5,222,959 A | 6/1993 | Anis |
| 5,242,385 A | 9/1993 | Strukel |
| 5,248,296 A | 9/1993 | Alliger |
| 5,267,954 A | 12/1993 | Nita |
| 5,269,297 A | 12/1993 | Weng et al. |
| 5,279,547 A | 1/1994 | Costin |
| 5,304,115 A | 4/1994 | Pflueger et al. |
| 5,312,329 A | 5/1994 | Beaty et al. |
| 5,318,570 A | 6/1994 | Hood et al. |
| 5,322,055 A | 6/1994 | Davison et al. |
| 5,331,951 A | 7/1994 | Kepley |
| 5,342,293 A | 8/1994 | Zanger |
| 5,359,996 A | 11/1994 | Hood |
| 5,364,405 A | 11/1994 | Zaleski |
| 5,382,228 A | 1/1995 | Nita et al. |
| 5,391,144 A | 2/1995 | Sakurai et al. |
| 5,397,293 A | 3/1995 | Alliger et al. |
| 5,397,301 A | 3/1995 | Pflueger et al. |
| 5,413,578 A | 5/1995 | Zahedi |
| 5,417,654 A | 5/1995 | Kelman |
| 5,431,664 A | 7/1995 | Ureche et al. |
| 5,451,220 A | 9/1995 | Ciervo |
| 5,451,230 A | 9/1995 | Steinert |
| 5,469,011 A | 11/1995 | Safabakhsh |
| 5,480,379 A | 1/1996 | La Rosa |
| 5,507,738 A | 4/1996 | Ciervo |
| 5,514,151 A | 5/1996 | Fogarty et al. |
| 5,520,633 A | 5/1996 | Costin |
| 5,527,273 A | 6/1996 | Manna et al. |
| 5,531,597 A * | 7/1996 | Foulkes et al. ............ 433/119 |
| 5,569,188 A | 10/1996 | Mackool |

(56) References Cited

U.S. PATENT DOCUMENTS

| | | |
|---|---|---|
| 5,591,127 A | 1/1997 | Barwick, Jr. et al. |
| 5,634,912 A | 6/1997 | Injev |
| 5,653,724 A | 8/1997 | Imonti |
| 5,669,922 A | 9/1997 | Hood |
| 5,676,649 A | 10/1997 | Boukhny et al. |
| 5,688,235 A | 11/1997 | Sakurai et al. |
| 5,690,641 A | 11/1997 | Sorensen et al. |
| 5,700,240 A | 12/1997 | Barwick, Jr. et al. |
| 5,722,945 A | 3/1998 | Anis et al. |
| 5,725,495 A | 3/1998 | Strukel et al. |
| 5,728,130 A | 3/1998 | Ishikawa et al. |
| 5,733,256 A | 3/1998 | Costin |
| 5,743,871 A | 4/1998 | Strukel et al. |
| 5,746,756 A | 5/1998 | Bromfield et al. |
| 5,766,146 A | 6/1998 | Barwick, Jr. |
| 5,776,155 A | 7/1998 | Beaupre et al. |
| 5,800,448 A | 9/1998 | Banko |
| 5,808,396 A | 9/1998 | Boukhny |
| 5,810,859 A | 9/1998 | DiMatteo et al. |
| 5,817,036 A | 10/1998 | Anthony et al. |
| 5,819,571 A | 10/1998 | Johnson |
| 5,825,118 A | 10/1998 | Okazaki |
| 5,865,790 A | 2/1999 | Bair |
| 5,879,364 A | 3/1999 | Bromfield et al. |
| 5,897,523 A | 4/1999 | Wright et al. |
| 5,904,690 A | 5/1999 | Middleman et al. |
| 5,921,999 A | 7/1999 | Dileo |
| 5,935,096 A | 8/1999 | Barrett |
| 5,938,633 A | 8/1999 | Beaupre |
| 5,938,677 A | 8/1999 | Boukhny et al. |
| 5,941,887 A | 8/1999 | Steen et al. |
| 5,944,737 A | 8/1999 | Tsonton et al. |
| 5,968,058 A | 10/1999 | Richter et al. |
| 5,971,949 A | 10/1999 | Levin et al. |
| 5,979,494 A | 11/1999 | Perkins et al. |
| 5,989,275 A | 11/1999 | Estabrook et al. |
| 5,993,409 A | 11/1999 | Maaskamp |
| 6,013,046 A | 1/2000 | Maaskamp et al. |
| 6,013,048 A | 1/2000 | Podany et al. |
| 6,024,750 A | 2/2000 | Mastri et al. |
| 6,027,515 A | 2/2000 | Cimino |
| 6,028,387 A | 2/2000 | Boukhny |
| 6,039,715 A | 3/2000 | Mackool |
| 6,053,906 A | 4/2000 | Honda et al. |
| 6,056,735 A | 5/2000 | Okada et al. |
| 6,063,050 A | 5/2000 | Manna et al. |
| 6,077,285 A | 6/2000 | Boukhny |
| 6,083,193 A | 7/2000 | Kadziauskas et al. |
| 6,159,175 A | 12/2000 | Strukel et al. |
| 6,171,265 B1 | 1/2001 | Novak et al. |
| 6,175,180 B1 | 1/2001 | Angelini et al. |
| 6,179,805 B1 | 1/2001 | Sussman et al. |
| 6,179,808 B1 | 1/2001 | Boukhny et al. |
| 6,193,683 B1 | 2/2001 | Ludin et al. |
| 6,206,844 B1 | 3/2001 | Reichel et al. |
| 6,217,543 B1 | 4/2001 | Anis et al. |
| 6,228,046 B1 | 5/2001 | Brisken |
| 6,238,386 B1 | 5/2001 | Muller et al. |
| 6,241,700 B1 | 6/2001 | Leukanech |
| 6,241,703 B1 | 6/2001 | Levin et al. |
| 6,251,110 B1 | 6/2001 | Wampler |
| 6,254,622 B1 | 7/2001 | Hood |
| 6,256,859 B1 | 7/2001 | Stoddard et al. |
| 6,258,053 B1 | 7/2001 | Mackool |
| 6,261,283 B1 | 7/2001 | Morgan et al. |
| 6,261,297 B1 | 7/2001 | Kadziauskas et al. |
| 6,278,218 B1 | 8/2001 | Madan et al. |
| 6,280,407 B1 | 8/2001 | Manna et al. |
| 6,283,974 B1 | 9/2001 | Alexander |
| 6,283,981 B1 | 9/2001 | Beaupre |
| 6,309,400 B2 | 10/2001 | Beaupre |
| 6,315,755 B1 | 11/2001 | Sussman |
| 6,325,811 B1 | 12/2001 | Messerly |
| 6,328,751 B1 | 12/2001 | Beaupre |
| 6,352,519 B1 | 3/2002 | Anis |
| 6,394,974 B1 | 5/2002 | Kadziauskas et al. |
| 6,400,648 B1 | 6/2002 | Heijnskijk et al. |
| 6,402,769 B1 | 6/2002 | Boukhny |
| 6,423,074 B1 | 7/2002 | Chen |
| 6,428,501 B1 | 8/2002 | Reynard |
| 6,432,118 B1 | 8/2002 | Messerly |
| 6,436,115 B1 | 8/2002 | Beaupre |
| 6,458,143 B1 | 10/2002 | Sugai |
| 6,468,286 B2 | 10/2002 | Mastri et al. |
| 6,475,224 B1 | 11/2002 | Pantages et al. |
| 6,478,766 B1 | 11/2002 | Chon |
| 6,491,661 B1 | 12/2002 | Boukhny et al. |
| 6,491,708 B2 | 12/2002 | Madan et al. |
| 6,494,868 B2 | 12/2002 | Amar |
| 6,514,267 B2 | 2/2003 | Jewett |
| 6,533,750 B2 | 3/2003 | Sutton et al. |
| 6,551,337 B1 | 4/2003 | Rabiner et al. |
| 6,561,983 B2 | 5/2003 | Cronin et al. |
| 6,585,745 B2 | 7/2003 | Cimino |
| 6,592,541 B1 | 7/2003 | Kurwa |
| 6,602,193 B2 | 8/2003 | Chon |
| 6,605,054 B2 | 8/2003 | Rockley |
| 6,629,948 B2 | 10/2003 | Rockley et al. |
| 6,660,017 B2 | 12/2003 | Beaupre |
| 6,679,899 B2 | 1/2004 | Wiener et al. |
| 6,682,544 B2 | 1/2004 | Mastri et al. |
| 6,695,782 B2 | 2/2004 | Ranucci et al. |
| 6,699,212 B1 | 3/2004 | Kadziauskas et al. |
| 6,736,835 B2 | 5/2004 | Pellegrino et al. |
| 6,752,815 B2 | 6/2004 | Beaupre |
| 6,773,444 B2 | 8/2004 | Messerly |
| 6,780,165 B2 | 8/2004 | Kadziauskas et al. |
| 6,811,553 B2 | 11/2004 | Anthone |
| 6,887,240 B1 | 5/2005 | Lands et al. |
| 6,893,434 B2 | 5/2005 | Fenton et al. |
| 6,898,536 B2 | 5/2005 | Wiener et al. |
| 6,923,421 B2 | 8/2005 | Raftis |
| 6,939,317 B2 * | 9/2005 | Zacharias ...................... 604/22 |
| 6,955,680 B2 | 10/2005 | Satou et al. |
| 6,976,969 B2 | 12/2005 | Messerly |
| 6,984,220 B2 | 1/2006 | Wuchinich |
| 7,014,629 B2 | 3/2006 | Mackool |
| 7,018,389 B2 | 3/2006 | Camerlengo |
| 7,019,234 B1 | 3/2006 | Mezhinsky et al. |
| 7,037,296 B2 | 5/2006 | Kadziauskas et al. |
| 7,163,548 B2 | 1/2007 | Stulen et al. |
| 7,185,555 B2 | 3/2007 | Peterson et al. |
| 7,229,455 B2 | 6/2007 | Sakurai et al. |
| 7,285,895 B2 | 10/2007 | Beaupre |
| 7,297,137 B2 | 11/2007 | Gordon et al. |
| 7,300,446 B2 | 11/2007 | Beaupre |
| 7,316,664 B2 | 1/2008 | Kadziauskas et al. |
| 7,335,997 B2 | 2/2008 | Wiener |
| 7,374,552 B2 | 5/2008 | Wuchinich |
| 7,443,296 B2 | 10/2008 | Mezhinsky et al. |
| 7,479,148 B2 | 1/2009 | Beaupre |
| 7,485,106 B2 | 2/2009 | Kadziauskas et al. |
| 7,530,986 B2 | 5/2009 | Beaupre et al. |
| 7,572,242 B2 | 8/2009 | Boukhny |
| 7,604,609 B2 | 10/2009 | Jervis |
| 7,621,930 B2 | 11/2009 | Houser |
| 7,625,388 B2 | 12/2009 | Boukhny et al. |
| 7,645,255 B2 | 1/2010 | Gordon et al. |
| 7,645,256 B2 | 1/2010 | Boukhny et al. |
| 7,651,490 B2 | 1/2010 | Boukhny et al. |
| 7,758,538 B2 | 1/2010 | Boukhny et al. |
| 7,713,202 B2 | 5/2010 | Boukhny et al. |
| 7,758,600 B2 | 7/2010 | Beaupre |
| 7,762,979 B2 | 7/2010 | Wuchinich |
| 7,794,414 B2 | 9/2010 | Rabiner et al. |
| 7,821,143 B2 | 10/2010 | Wiener |
| 8,016,843 B2 | 9/2011 | Escaf |
| 8,021,381 B2 | 9/2011 | Beaupre |
| 8,057,498 B2 | 11/2011 | Robertson |
| 8,058,771 B2 | 11/2011 | Giordano et al. |
| 8,152,825 B2 | 4/2012 | Madan et al. |
| 8,172,786 B2 | 5/2012 | Boukhny |
| 8,183,022 B2 | 5/2012 | Steiner |
| 8,241,312 B2 | 8/2012 | Messerly |

(56) References Cited

U.S. PATENT DOCUMENTS

| | | | |
|---|---|---|---|
| 8,252,012 B2 | 8/2012 | Stulen | |
| 8,253,303 B2 | 8/2012 | Giordano et al. | |
| 8,348,880 B2 | 1/2013 | Messerly et al. | |
| 8,623,040 B2* | 1/2014 | Artsyukhovich | A61F 9/00745 604/22 |
| 9,233,021 B2 | 1/2016 | Artsyukhovich et al. | |
| 2001/0025184 A1 | 9/2001 | Messerly | |
| 2001/0027601 A1 | 10/2001 | Stoddard et al. | |
| 2001/0034532 A1 | 10/2001 | Cimino | |
| 2002/0072754 A1 | 6/2002 | Camerlengo | |
| 2002/0128674 A1 | 9/2002 | Beaupre | |
| 2003/0045887 A1 | 3/2003 | Sakurai et al. | |
| 2003/0065263 A1 | 4/2003 | Hare et al. | |
| 2003/0093099 A1 | 5/2003 | Anthone | |
| 2003/0125620 A1 | 7/2003 | Satou et al. | |
| 2003/0164659 A1 | 9/2003 | Iino et al. | |
| 2003/0212331 A1 | 11/2003 | Fenton et al. | |
| 2004/0056220 A1 | 3/2004 | Raftis | |
| 2004/0092800 A1 | 5/2004 | MacKool | |
| 2004/0092922 A1 | 5/2004 | Kadziauskas et al. | |
| 2004/0127887 A1 | 7/2004 | Zinkel | |
| 2004/0127926 A1 | 7/2004 | Beaupre | |
| 2004/0162571 A1 | 8/2004 | Rabiner et al. | |
| 2004/0193104 A1 | 9/2004 | Jervis | |
| 2004/0193121 A1 | 9/2004 | Kadziauskas et al. | |
| 2004/0199192 A1 | 10/2004 | Akahoshi | |
| 2004/0210140 A1 | 10/2004 | Rabiner et al. | |
| 2004/0215127 A1 | 10/2004 | Kadziauskas et al. | |
| 2005/0043671 A1 | 2/2005 | Rockley et al. | |
| 2005/0049546 A1 | 3/2005 | Messerly et al. | |
| 2005/0070939 A1 | 3/2005 | Beaupre | |
| 2005/0075656 A1 | 4/2005 | Beaupre | |
| 2005/0187513 A1* | 8/2005 | Rabiner et al. | 604/22 |
| 2005/0209621 A1 | 9/2005 | Gordon et al. | |
| 2005/0228425 A1 | 10/2005 | Boukhny et al. | |
| 2005/0234473 A1 | 10/2005 | Zacharias | |
| 2005/0234484 A1 | 10/2005 | Houser et al. | |
| 2005/0261628 A1 | 11/2005 | Boukhny et al. | |
| 2005/0261715 A1 | 11/2005 | Boukhny et al. | |
| 2005/0267504 A1 | 12/2005 | Boukhny et al. | |
| 2005/0273126 A1 | 12/2005 | Beaupre | |
| 2005/0277869 A1 | 12/2005 | Boukhny | |
| 2006/0036180 A1 | 2/2006 | Boukhny et al. | |
| 2006/0041220 A1 | 2/2006 | Boukhny et al. | |
| 2006/0079978 A1 | 4/2006 | Anderson et al. | |
| 2006/0084963 A1 | 4/2006 | Messerly | |
| 2006/0100616 A1 | 5/2006 | Beaupre | |
| 2006/0129140 A1 | 6/2006 | Todd et al. | |
| 2006/0135975 A1 | 6/2006 | Perkins | |
| 2006/0145540 A1 | 7/2006 | Mezhinsky | |
| 2006/0189948 A1* | 8/2006 | Boukhny | 604/272 |
| 2006/0190003 A1 | 8/2006 | Boukhny et al. | |
| 2006/0211943 A1 | 9/2006 | Beaupre | |
| 2006/0217672 A1 | 9/2006 | Chon | |
| 2006/0217739 A1 | 9/2006 | Tjia et al. | |
| 2006/0264970 A1 | 11/2006 | Ernest et al. | |
| 2007/0016236 A1 | 1/2007 | Beaupre | |
| 2007/0060926 A1 | 3/2007 | Escaf | |
| 2007/0073325 A1 | 3/2007 | Stulen et al. | |
| 2007/0129723 A1 | 6/2007 | Houser et al. | |
| 2007/0191713 A1 | 8/2007 | Eichmann et al. | |
| 2007/0239025 A1 | 10/2007 | Wiener et al. | |
| 2007/0255196 A1 | 11/2007 | Wuchinich | |
| 2007/0260173 A1 | 11/2007 | Boukhny et al. | |
| 2007/0260200 A1 | 11/2007 | Boukhny et al. | |
| 2008/0051814 A1 | 2/2008 | Beaupre | |
| 2008/0058708 A1 | 3/2008 | Akahoshi | |
| 2008/0103418 A1 | 5/2008 | Wuchinich | |
| 2008/0139994 A1 | 6/2008 | Mackool et al. | |
| 2008/0200940 A1 | 8/2008 | Eichmann et al. | |
| 2008/0234710 A1 | 9/2008 | Neurohr et al. | |
| 2008/0281253 A1 | 11/2008 | Injev et al. | |
| 2008/0294087 A1 | 11/2008 | Steen et al. | |
| 2008/0300611 A1 | 12/2008 | Houser et al. | |
| 2009/0005712 A1 | 1/2009 | Raney | |
| 2009/0030311 A1 | 1/2009 | Stulen et al. | |
| 2009/0030437 A1 | 1/2009 | Houser et al. | |
| 2009/0030439 A1 | 1/2009 | Stulen | |
| 2009/0036911 A1 | 2/2009 | Stulen | |
| 2009/0036913 A1 | 2/2009 | Wiener et al. | |
| 2009/0036914 A1 | 2/2009 | Houser | |
| 2009/0066192 A1 | 3/2009 | Taki et al. | |
| 2009/0093750 A1 | 4/2009 | Herman | |
| 2009/0131885 A1* | 5/2009 | Akahoshi | 604/272 |
| 2009/0131962 A2 | 5/2009 | Houser et al. | |
| 2009/0143795 A1 | 6/2009 | Robertson | |
| 2009/0143806 A1 | 6/2009 | Witt et al. | |
| 2009/0236938 A1* | 9/2009 | Bromfield | B06B 1/0611 310/323.19 |
| 2009/0264909 A1 | 10/2009 | Beaupre | |
| 2009/0264910 A1 | 10/2009 | Laufer | |
| 2009/0270891 A1* | 10/2009 | Beaupre | A61B 17/320092 606/169 |
| 2010/0004585 A1 | 1/2010 | Boukhny et al. | |
| 2010/0004586 A1 | 1/2010 | Boukhny | |
| 2010/0010419 A1 | 1/2010 | Akahoshi | |
| 2010/0036256 A1 | 2/2010 | Boukhny et al. | |
| 2010/0042126 A1 | 2/2010 | Houser et al. | |
| 2010/0057118 A1 | 3/2010 | Dietz et al. | |
| 2010/0063525 A1 | 3/2010 | Beaupre et al. | |
| 2010/0063526 A1 | 3/2010 | Beaupre et al. | |
| 2010/0063527 A1 | 3/2010 | Beaupre et al. | |
| 2010/0063528 A1 | 3/2010 | Beaupre | |
| 2010/0069825 A1 | 3/2010 | Raney | |
| 2010/0069828 A1 | 3/2010 | Steen et al. | |
| 2010/0087758 A1 | 4/2010 | Beaupre et al. | |
| 2010/0087846 A1 | 4/2010 | Dimalanta | |
| 2010/0094321 A1 | 4/2010 | Akahoshi et al. | |
| 2010/0106173 A1 | 4/2010 | Yoshimine | |
| 2010/0331743 A1 | 4/2010 | Beaupre et al. | |
| 2010/0262172 A1 | 10/2010 | Houser et al. | |
| 2010/0324581 A1 | 12/2010 | Mackool et al. | |
| 2010/0331869 A1 | 12/2010 | Voegele et al. | |
| 2010/0331870 A1 | 12/2010 | Wan et al. | |
| 2010/0331871 A1 | 12/2010 | Nield et al. | |
| 2010/0331872 A1 | 12/2010 | Houser et al. | |
| 2011/0004149 A1 | 1/2011 | Artsyukhovich et al. | |
| 2011/0009374 A1 | 1/2011 | Keller | |
| 2011/0015561 A1 | 1/2011 | Akahoshi | |
| 2011/0015658 A1 | 1/2011 | Vijfvinkel | |
| 2011/0082486 A1 | 4/2011 | Messerly et al. | |
| 2011/0087212 A1 | 4/2011 | Aldridge et al. | |
| 2011/0087213 A1 | 4/2011 | Messerly et al. | |
| 2011/0087214 A1 | 4/2011 | Giordano et al. | |
| 2011/0087215 A1 | 4/2011 | Aldridge et al. | |
| 2011/0087217 A1 | 4/2011 | Yates et al. | |
| 2011/0087256 A1 | 4/2011 | Wiener et al. | |
| 2011/0166502 A1 | 7/2011 | Nallakrishnan | |
| 2011/0172588 A1 | 7/2011 | Akahoshi | |
| 2011/0196287 A1 | 8/2011 | Robertson et al. | |
| 2011/0196403 A1 | 8/2011 | Robertson et al. | |
| 2011/0196404 A1 | 8/2011 | Dietz et al. | |
| 2011/0288452 A1 | 11/2011 | Houser et al. | |
| 2011/0319918 A1 | 12/2011 | Beaupre | |
| 2012/0010537 A1 | 1/2012 | Young et al. | |
| 2012/0029546 A1 | 2/2012 | Robertson | |
| 2012/0072197 A1 | 3/2012 | Ovchinnikov | |
| 2012/0078139 A1 | 3/2012 | Aldridge et al. | |
| 2012/0123458 A1 | 5/2012 | Giordano et al. | |
| 2012/0197215 A1 | 8/2012 | Akahoshi | |
| 2012/0323265 A1 | 12/2012 | Stulen | |
| 2012/0330338 A1 | 12/2012 | Messerly | |
| 2013/0035706 A1 | 2/2013 | Giordano et al. | |
| 2013/0035707 A1 | 2/2013 | Giordano et al. | |

FOREIGN PATENT DOCUMENTS

| | | |
|---|---|---|
| DE | 203229 C | 10/1908 |
| DE | 203229 B3 | 10/1983 |
| DE | 3416490 C1 | 2/1986 |
| DE | 3624243 A1 | 1/1988 |
| DE | 8816114 U1 | 2/1989 |
| DE | 4012882 A1 | 10/1991 |
| DE | 10146011 A1 | 4/2003 |

(56) References Cited

FOREIGN PATENT DOCUMENTS

| | | |
|---|---|---|
| EP | 269870 A1 | 6/1988 |
| EP | 0359217 A2 | 3/1990 |
| EP | 0456470 A1 | 11/1991 |
| EP | 0482847 A1 | 4/1992 |
| EP | 0514810 A1 | 5/1992 |
| EP | 0674350 A1 | 9/1995 |
| EP | 0830845 A1 | 3/1998 |
| EP | 0968684 A1 | 1/2000 |
| EP | 970659 A1 | 1/2000 |
| EP | 970660 A1 | 1/2000 |
| EP | 0830845 B1 | 8/2003 |
| EP | 1693027 A1 | 8/2006 |
| EP | 970659 B1 | 10/2006 |
| EP | 970660 B1 | 10/2006 |
| EP | 0968684 B1 | 12/2006 |
| EP | 1852096 A1 | 11/2007 |
| EP | 1693027 B1 | 7/2008 |
| EP | 1990032 | 11/2008 |
| EP | 2322106 A2 | 5/2011 |
| EP | 2322106 A3 | 3/2012 |
| ES | 2116203 A1 | 7/1998 |
| ES | 2116203 B1 | 2/1999 |
| FR | 2641693 | 7/1990 |
| FR | 2707872 | 1/1995 |
| GB | 2032221 A | 4/1980 |
| GB | 2176110 A | 12/1986 |
| GB | 2247174 A | 2/1992 |
| GB | 2365775 A | 2/2002 |
| GB | 2374290 A | 10/2002 |
| JP | S59-24013 | 2/1984 |
| JP | 62136398 A | 6/1987 |
| JP | 62-207450 A | 9/1987 |
| JP | 63111115 U | 7/1988 |
| JP | 63236577 A | 10/1988 |
| JP | 63-305856 A | 12/1988 |
| JP | 01027549 A | 1/1989 |
| JP | 03021232 A | 1/1991 |
| JP | U H05 62225 | 8/1993 |
| JP | 7110277 B | 11/1995 |
| JP | H09-313496 | 12/1997 |
| JP | 2000-070279 A | 3/2000 |
| JP | 2001-061847 | 3/2001 |
| JP | 2001178736 A | 7/2001 |
| JP | 2003033364 A2 | 2/2003 |
| JP | 2003116870 | 4/2003 |
| JP | 2006-223865 | 8/2006 |
| JP | 09009656 | 1/2009 |
| NL | 2001401 C2 | 9/2009 |
| RU | 2167635 C2 | 5/2001 |
| RU | 62013 U1 | 3/2007 |
| RU | 64054 U1 | 6/2007 |
| SU | 1000028 | 2/1983 |
| SU | 1026793 A1 | 7/1983 |
| SU | 1695900 A1 | 12/1991 |
| WO | WO 86/02257 A1 | 4/1986 |
| WO | 87/05793 A1 | 10/1987 |
| WO | 92/07622 A1 | 5/1992 |
| WO | 93/14709 A1 | 8/1993 |
| WO | WO 94/08518 A1 | 4/1994 |
| WO | WO 95/10233 A1 | 4/1995 |
| WO | 95/20374 A1 | 8/1995 |
| WO | WO 96/35923 A2 | 11/1996 |
| WO | WO 96/35923 A3 | 3/1997 |
| WO | WO 1998/023212 A1 | 6/1998 |
| WO | WO 1998/35721 A2 | 8/1998 |
| WO | WO 1998/35721 A3 | 10/1998 |
| WO | 99/18901 A1 | 4/1999 |
| WO | 99/35982 A1 | 7/1999 |
| WO | 99/45868 A1 | 9/1999 |
| WO | 00/48520 A1 | 8/2000 |
| WO | 01/24744 A1 | 4/2001 |
| WO | 01/41672 A2 | 6/2001 |
| WO | 01/52782 A1 | 7/2001 |
| WO | 01/41672 A3 | 12/2001 |
| WO | 01/97728 A1 | 12/2001 |
| WO | 02/17833 A1 | 3/2002 |
| WO | 02/26016 A2 | 4/2002 |
| WO | 02/056806 A1 | 7/2002 |
| WO | 02/083010 A1 | 10/2002 |
| WO | 03/043550 A1 | 5/2003 |
| WO | 03/095028 A1 | 11/2003 |
| WO | 2004/080505 A2 | 9/2004 |
| WO | 2004/080505 A3 | 7/2005 |
| WO | 2005/084552 A1 | 9/2005 |
| WO | 2005/084553 A1 | 9/2005 |
| WO | 2005/092022 A2 | 10/2005 |
| WO | 2005/092023 A2 | 10/2005 |
| WO | WO 2007/119107 A2 | 10/2007 |
| WO | WO 2007/119107 A3 | 12/2007 |
| WO | WO 2008/065323 A1 | 6/2008 |
| WO | WO 2009/120075 A1 | 10/2009 |
| WO | WO 2010/089629 A2 | 8/2010 |
| WO | WO 2010/093347 A1 | 8/2010 |
| WO | WO 11/002576 A1 | 1/2011 |
| WO | WO 2012/036795 A2 | 3/2012 |
| WO | WO 2012/036795 A3 | 7/2012 |

OTHER PUBLICATIONS

International Searching Authority, Written Opinion of the International Searching Authority, International Application No. PCT/US2011/046362, dated Mar. 16, 2012, 5 pages.

Adams, Maurice L., Jr., Rotating Machinery Vibration, From Analysis to Troubleshooting, book, © 2001, 29 pages, Marcel Dekker, Inc., New York, NY.

Alterman, Z., et al., Propagation of Elastic Waves in a Semi-Infinite Cylindrical Rod Using Finite Difference Methods, J. Sound Vib., 1970, pp. 115-145, vol. 13 (2).

Bert, C.W., et al., Whirling of Composite-Material Driveshafts including Bending-Twisting Coupling and Transverse Shear Deformation, Journal of Vibration and Acoustics, Jan. 1995, pp. 17-21, vol. 117.

Bhaskar, Atula, Waveguide modes in elastic rods, Mathmatical, Physical & Engineering Sciences, Nov. 14, 2002, pp. 175-194, vol. 459, Royal Society Publishing, UK.

Bishop, R.E.D., et al., On Coupled Bending and Torsional Vibration of Uniform Beams, Journal of Sound and Vibration, 1989, vol. 131(3), pp. 457-464, Brunel University, Uxbridge, England.

Cascante, Giovanni, et al., Flexural excitation in a standard torsional-resonant column device, Can Geotech. J., 1998, pp. 478-490, vol. 35, NRC Canada.

Cheng, J.K., et al., Stability and Nonlinear Dynamics of a Horizontally Base-Excited Rigid Rod with Unsymmetric End Stiffnesses, Journal of Vibration and Acoustics, Jan. 1993, pp. 85-95, vol. 115.

Cohen, R., et al., Coupled Torsional and Transverse Vibration of Unbalanced Rotor, Journal of Applied Mechanics, Sep. 1985, pp. 701-705, vol. 52.

Designer.K, et al., A New Application System for Laser and Ultrasonic Therapy in Endoscopic Surgery, SPIE, 1996, pp. 268-274, vol. 2922.

Dokumaci. E, An Exact Solution for Coupled Bending and Torsion Vibrations of Uniform Beams Having Single Cross-Sectional Symmetry, Journal of Sound and Vibration, 1987, pp. 443-449, vol. 119(3), Academic Press Limited.

Dunn, D.J., Solid Mechanics Dynamics Tutorial—forced Vibrations, downloaded from http://web.archive.org/web/20070906003853/http://www.freestudy.co.us/dynamics/, archive dated Sep. 6, 2007, filed dated May 4, 2007, pp. 1-18.

Etneir, Shelley A., Twisting and Bending of Biological Beams: Distribution of Biological Beams in a Stiffness Mechanospace, Biol. Bull., Aug. 2003, pp. 36-46, vol. 205, Marine Biological Laboratory, Durham, North Carolina.

Friend, James R., et al., A Novel Torsional Microtransducer Using Bulk PZT, 2002 IEEE Ultrasonics Symposium, pp. 1123-1126, Tokyo Institute of Technology, Yokohama, Japan.

Golyamina, I.P., et al., Ultrasonic Vibratory Systems with a Curved Working Section, Sov. Phys. Acoust., Mar.-Apr. 1990, pp. 135-138, vol. 36(2), American Institute of Physics.

(56) References Cited

OTHER PUBLICATIONS

Gregory, R.D., et al., Axisymmetric Waves in a Semi-Infinite Elastic Rod, Q.Jl Mech. App. Math., 327-337, vol. 42, Pt. 2, Oxford University Press 1989.
Haeggstrom, Edward, et al., Capacitive Micromachined Ultrasonic Transducer Based Integrated Actuator for Atomic Force Microscope Cantilevers, IEEE-NANO, Aug. 26, 2002, pp. 45-49.
Ilanko, S., Whirling Speed of Shafts, 2005, pp. 64-65.
International Searching Authority, Written Opinion of the International Searching Authority, International Application No. PCT/US10/37610, dated Sep. 16, 2010, 7 pages.
Kim, Yong Y., Flexural-Torsional Coupled Vibration of Rotating Beams Using Orthogonal Polynomials, Thesis submitted to the Faculty of the Virginia Polytechnic Institute and State University, May 1, 2000, 117 pages, Blacksburg, Virginia.
Kuwahara, Yasuhara, Aspiration Method of a Hard Cataract, book, 1972, pp. 1-15, 31-75 and 96-115, Igaku Shoin Ltd., Tokyo, Japan.
Allen, Henry F. reviewing Aspiration Method of a Hard Cataract: Ultrasonic Vibration by Yasuharu Kuwahara, Arch Ophthalmol., Sep. 1973, p. 260, vol. 90.
Kuwahara, Yasuharu, Aspiration Method of Senile Cataract, Keio J. Med., Jun. 18, 1970, pp. 115-133, vol. 19, Tokyo, Japan.
Kuwahara, Yasuharu, Aspiration Method of Senile Cataract, Keio J. Med., May-Jun. 1971, pp. 97-107, vol. 2, No. 3, Tokyo, Japan.
Lee, Jaehong, et al., Flexural-torsional behavior of thin-walled composite beams, Thin Walled Structures, 2004, pp. 1293-1305, vol. 42, Elsevier Ltd., South Korea.
Love, A.E.H., A Treatise on the Mathematical Theory of Elasticity, 1920, Third Edition, pp. i-vi, 281-296, 315-333, and 387-460.
Mao, Cheng, et al., Coupled Torsional-Flexural Vibration of Shaft Systems in Mechanical Engineering-II. Fe—Tm Impedance Coupling Method, Computers and Structures, 1996, pp. 845-849, vol. 58, No. 4, Elsevier Science, Ltd., Great Britain.
Mitaku, Shigeki, et al., Composite torsional quartz transducer for shear ultrasonic measurements of aqueous liquids, Rev. Sci. Instrum., 1979, pp. 1437-1440, vol. 50, No. 11, American Institute of Physics.
Nicholson, N.C., et al., Mode propagation of ultrasound in holow waveguides, Ultrasonics, 1991, pp. 411-416, vol. 29.
Oliver, Jack, Elastic Wave Dispersion in a Cylindrical Rod by a Wide-Band Short-Duration Pulse Technique*, The Journal of the Acoustical Society of America, Feb. 1957, pp. 189-194, vol. 29, No. 2.
Onaran, A. Guclu, et al., Tapping mode and elasticity imaging in liquids using an atomic force microscope actuated by acoustic radiation pressure, Applied Physics Letters, May 27, 2002, pp. 4063-4065, vol. 80, No. 21, American Institute of Physics.
Phillips, J.W., et al., On the Theory of Pulse Propagation in Curved Beams, Journal of Sound and Vibration, 1972, pp. 247-258, vol. 24(2).
Plaut, R.H., et al., Parametric, External and Comvination Resonances in Coupled Flexural and Torsional Oscillations of an Unbalanced Rotating Shaft, Journal of Sound and Vibration, 1995, pp. 889-897, vol. 183(5).
Qin, Qing Hua, et al., Coupled Torsional-Flexural Vibration of Shaft Systems in Mechanical Engineering-I. Finite Element Model, Computers and Structures, 1996, pp. 835-843, vol. 58, No. 4, Elsevier Science Ltd., Great Britain.
Rabe, U., et al., Vibrations of free and surfacecoupled atomic force microscope cantilevers: Theory and experiment, Review of Scientific Instruments, 1996, pp. 3281-3293 vol. 67, No. 9, American Institute of Physics.
Rees, David W., Mechanics of Solids and Structures, Chapter 5: Theories of Torsion, 2000, pp. 197-252.
Rossing, Thomas D., et al., Laboratory observation of elastic waves in solids, Am. J. Phys., Dec. 1990, pp. 1153-1162, vol. 58, No. 12.
Russell, Daniel A., Vibrational Behavior of a Hockey Stick, © 2004-2011, 3 pages.
Sandor, Bela I., et al., Mechanics of Solids, 1999, 9 pages, CRC Press, LLC.

Satonobu, et al., Traveling Wave Excitation in a Flexural Vibration Ring by Using a Torsional-Flexural Composite Tranducer, IEEE Transactions on Ultrasonics, Ferroelectrics, and Frequency Control, Jul. 2001, pp. 1054-1059, vol. 48, No. 4.
Sazonov, I.A., Features of the Vibration of Curved Sectional Roads in Ultrasonic Oscillating Systems, Acoustics Institute, Moscow, Jun. 1989, pp. 62-68, vol. 25, No. 6, Plenum Publishing Corporation.
Sazonov, I.A., Selection of the centroidal line in curved beams of variable cross section, Sov. Phys. Acoust., 1990, pp. 298-301, vol. 36(3).
Sazonov, I.A., Wave propagation in curved rods of variable cross section, Sov. Phys. Acoust., Mar.-Apr. 1977, pp. 163-167, vol. 23, No. 2.
Shuyu, Lin, Sandwiched Piezoelectric Ultrasonic Transducers of Longitudinal-Torsional Compound Vibrational Modes, IEEE Transactions of Ultrasonics, Ferroelectrics, and Frequency Control, Nov. 1997, pp. 1189-1197, vol. 44, No. 6.
Shuyu, Lin, Study on the prestressed sandwich piezoelectric ceramic ultrasonic transducer of torsional-flexural composite vibrational mode, J. Acoust. Soc. Am., Aug. 2002, pp. 511-517, vol. 112, No. 2.
Steinert, Roger F., Cataract Surgery, Chapter 17: Phaco Chop, 2010, pp. 205-213, Third Edition, Elsevier.
Steinert, Roger F., et al., Cataract Surgery, Chapter 7: The Phaco Machine: The Physical Principles Guiding its Operation, 2010, pp. 75-92, Third Edition, Elsevier.
Togawa, et al., Application of Ultrasonic Instruments to Physiological Experiments, pp. 43-46, 1992.
Tso, W.K., On the Motion of a Curved and Twisted Rod, Acta Mechanica, 1972, pp. 163-178, vol. 13, Springer-Verlal.
Tsujino, J., et al., Transverse and torsional complex vibration systems for ultrasonic seam welding of metal plates, Ultrasonics, 2000, pp. 67-71, vol. 38, Elsevier Science B.V.
Tsujino, Jiromaru, Ultrasonic Motor Using a One-Dimensional Longitudinal-Torsional Vibration Converter with Diagonal Slits, Smart Mater. Struct. 7, 1998, pp. 345-351.
Vandiver, Kim J., et al., Case Studies of the Bending Vibration and Whirling Motion of Drill Collars, SPE Drilling Engineering, Dec. 1990, pp. 282-290, vol. 5, No. 4, Society of Petroleum Engineers.
Zhou, Guangping, et al., The complex-mode vibration of ultrasonic vibration systems, Ultrasonics, 2002, pp. 907-911, vol. 40, Elsevier Science B.V.
European Patent Office, Supplementary European Search Report, Application No. 11825599.1, Publication No. 2616024, Published Jul. 24, 2013, 6 pages.
Severson, Ryan J., Office Action, U.S. Appl. No. 11/060,827, dated Mar. 11, 2008, 6 pages.
Severson, Ryan J., Office Action, U.S. Appl. No. 11/060,827, dated Mar. 20, 2007, 8 pages.
Severson, Ryan J., Office Action, U.S. Appl. No. 11/060,827, dated May 11, 2009, 11 pages.
Severson, Ryan J., Office Action, U.S. Appl. No. 11/060,827, dated May 30, 2007, 6 pages.
Severson, Ryan J., Office Action, U.S. Appl. No. 11/060,827, dated Jun. 27, 2007, 6 pages.
Severson, Ryan J., Office Action, U.S. Appl. No. 11/060,827, dated Aug. 17, 2009, 8 pages.
Severson, Ryan J., Office Action, U.S. Appl. No. 11/060,827, dated Sep. 19, 2007, 9 pages.
Severson, Ryan J., Office Action, U.S. Appl. No. 11/060,827, dated Nov. 10, 2008, 7 pages.
Severson, Ryan J., Office Action, U.S. Appl. No. 11/060,827, dated May 30, 2008, 6 pages.
Eastwood, David C., Office Action, U.S. Appl. No. 11/232,205, dated Feb. 27, 2009, 5 pages.
Eastwood, David C., Office Action, U.S. Appl. No. 11/232,205, dated Jun. 23, 2009, 7 pages.
Eastwood, David C., Office Action, U.S. Appl. No. 11/232,205, dated Oct. 19, 2009, 6 pages.
Abstract of JP 63305856 A, Dec. 12, 1988, Olympus Optical Co.
Dimalanta, Ramon C., "Extended Point Phacoemulsification Tip," U.S. Appl. No. 12/616,537, filed Nov. 11, 2009, 27 pages.

(56) References Cited

OTHER PUBLICATIONS

Artsyukhovich, Alex, et al., "Phacoemulsification Hook Tip," U.S. Appl. No. 12/496,220, filed Jul. 1, 2009, 20 pages.
Astashev, V.K., et al., "Ultrasonic cutting as a nonlinear (vibro-impact) process," Ultrasonics, vol. 36 (1998), pp. 89-96.
Obazawa, Hajime, et al., "Studies on the Influence of Various Ultrasonic Characters on Phacoemulsification Effects," Aug. 10, 1969, 135-153, 73(8), Nichigankaishi, Shinjuku-ku, Tokyo.
Thoe, T.B., et al., "Review of Ultrasonic Machining," Int. J. Mach. Tools Manufact., vol. 38, No. 4, pp. 239-255, 1998.
Graff, K.F., "Process Applications of Power Ultrasonics—A Review," IEEE Ultrasonics Symposium Proceedings, Cat. #74, CH)896-ISU, 1974.
Markov, A.L., "The Calculation and Design of Vibrators for Ultrasonic Machining," Soviet Progress in Apppplied Ultrasonics, vol. 1—Ultrasound in Industrial Processing and Control; Edited by V.F. Nozdreva Authorized translation from the Russian; Consultants Bureau, New York, 1964.
Smith, W.M.R., et al., "Factors in the design of ultrasonic probes," Ultrasonics, vol. 17, Issue 1, Jan. 1979, pp. 20-26.
"Phacoemulsification Tip Technology Guide," Alcon brochure, Dec. 2009, 8 pages.

\* cited by examiner

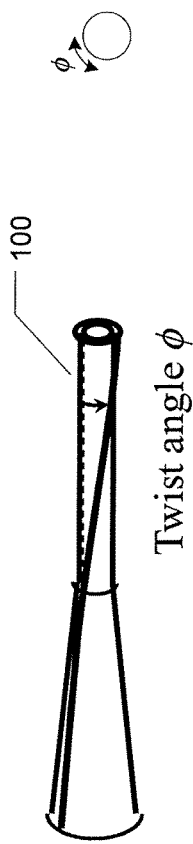

Twist angle $\phi$

Straight tip $$\ddot{\phi} = \frac{1}{\rho I(z)} \frac{\partial}{\partial z}\left( C(z) \frac{\partial \phi}{\partial z} \right)$$

Curved tip $$\ddot{\phi} = \frac{1}{\rho I(z)} \frac{\partial}{\partial z}\left( C(z) \frac{\partial \phi}{\partial z} \right) - \frac{d^2 I(z)}{dz^2}\left( EI_y(z) \left( \frac{d^2 u_x}{dz^2} - \phi \frac{d^2 I(z)}{dz^2} \right) \right)$$

$$\ddot{\phi} = \frac{\partial^2 \phi}{\partial t^2} \qquad I(z) = \frac{\pi}{2}\left( R_2^4(z) - R_1^4(z) \right) \qquad C(z) = I(z) * \mu$$

FIG. 7a

Lateral displacement $u_x$

Straight tip

$$\ddot{u}_x = \frac{1}{\rho S(z)} \frac{d^2}{dz^2}\left(EI_y(z)\frac{d^2 u_x}{dz^2}\right)$$

Curved tip

$$\ddot{u}_x = \frac{1}{\rho S(z)} \frac{d^2}{dz^2}\left(EI_y(z)\left(\frac{d^2 u_x}{dz^2} - \phi\frac{d^2 l(z)}{dz^2}\right)\right)$$

$$\ddot{u}_x = \frac{\partial^2 u_x}{\partial t^2} \qquad I_y(z) = \frac{\pi}{4}\left(R_2^4(z) - R_1^4(z)\right)$$

$$S(z) = \pi\left(R_2^2(z) - R_1^2(z)\right)$$

Input: Tip Shape

Output: Displacements of Twisting Mode

| Balanced Tip | OD | ID | L | $L_c$ | $x_1$ | $x_2$ | $\alpha_1$ | $y_1$ | $y_1'$ | $\alpha_2$ | Bevel |
|---|---|---|---|---|---|---|---|---|---|---|---|
| Tip 1 | .033 | .0225 | 1.174 | .308 | .252 | .153 | -19 | .152 | .055 | 37 | Up 30 or 45 degrees |
| Tip 2 | .033 | .0225 | 1.175 | .308 | .258 | .155 | -19 | .154 | .060 | 36 | Down 30 degrees |
| Tip 3 | .0315 | .0225 | 1.175 | .308 | .252 | .153 | -19 | .152 | .058 | 36 | Up 30 or 45 degrees |
| Tip 4 | .0315 | .0225 | 1.185 | .308 | .252 | .153 | -19 | .152 | .058 | 36 | Down 30 degrees |
| Tip 5 | .028 | .020 | 1.177 | .312 | .238 | .121 | -12 | .121 | .043 | 27 | Up 30 or 45 degrees |
| Tip 6 | .028 | .020 | 1.187 | .312 | .244 | .127 | -12 | .127 | .049 | 27 | Down 30 degrees |

*FIG. 11*

BALANCED PHACOEMULSIFICATION TIP

FIELD OF THE INVENTION

The present invention generally pertains to phacoemulsification. More particularly, but not by way of limitation, the present invention pertains to phacoemulsification tips.

DESCRIPTION OF THE RELATED ART

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an intraocular lens (IOL).

Cataractous lenses may be removed by a surgical technique called phacoemulsification. During this procedure, a thin phacoemulsification tip may be inserted into the diseased lens and vibrated ultrasonically. The vibrating tip may liquefy or emulsify the lens so that the lens may be aspirated out of the eye. The diseased lens, once removed, may be replaced by an artificial lens.

SUMMARY OF THE INVENTION

In various embodiments, a phacoemulsification tip may include a shaft and a cutting edge portion having at least a first and second bend. The geometry of the shaft and the at least first and second bend may be configured to result in a lateral displacement, perpendicular to the shaft during ultrasonic torsional vibration of the tip, of the shaft along its length that is less than approximately 5% to 25% (e.g., 15%) (other thresholds may also be used) of the displacement of the distal end point of the tip. In some embodiments, the shaft may extend from the end of a conical portion (which may be, for example, approximately 12 mm from the distal end point of the tip) through to the first bend in the cutting edge portion (which may be, for example, approximately 5 mm from the distal end point of the tip). Other locations of the first bend are also contemplated (e.g., 3 mm, 8 mm, etc. from the distal end point of the tip). In some embodiments, a proximal end of the conical portion (i.e., the hub) may be configured to couple to an ultrasonic horn.

In some embodiments, a method of determining a tip geometry may include providing two or more tip geometries (e.g., in an electronic format such as a computer readable input file with one or more stored variables describing the geometry), modeling behavior of the tip geometries during ultrasonic torsional vibrations and comparing lateral displacement of the various tip geometries to select a tip with a smallest lateral displacement along a portion of the tip shaft configured to be along an incision in an eye during a phacoemulsification procedure (which may be, for example, from an end of the conical portion to the first bend).

In some embodiments, a method of determining a tip geometry may include providing two or more physical tips with different geometries (e.g., hand bent at two or more locations along the tip), ultrasonically torsionally vibrating the different tips, determining lateral displacement of the various tips, and comparing the determined lateral displacements to select a tip with a smallest lateral displacement along a portion of the tip shaft configured to be along an incision in an eye during a phacoemulsification procedure.

BRIEF DESCRIPTION OF THE DRAWINGS

For a more complete understanding of the present invention, reference is made to the following description taken in conjunction with the accompanying drawings in which:

FIG. 7a illustrates model equations for twist displacement along the z axis of the tip, according to an embodiment;

FIG. 11 illustrates six possible balanced tip embodiments.

It is to be understood that both the foregoing general description and the following detailed description are exemplary and explanatory only and are intended to provide a further explanation of the present invention as claimed.

DETAILED DESCRIPTION OF THE EMBODIMENTS

Figure 1:
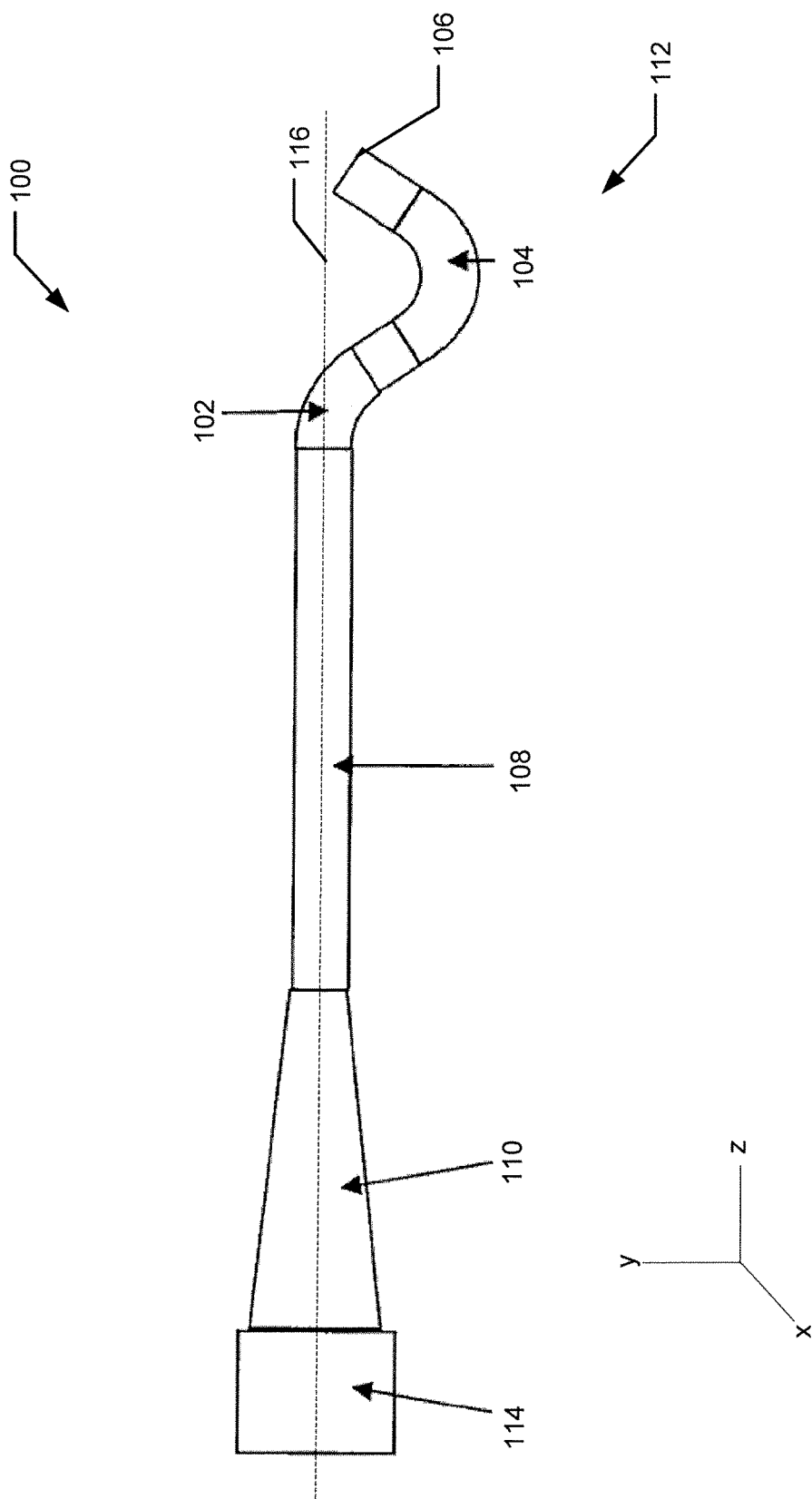
FIG. 1 illustrates a balanced phacoemulsification tip with a distal end having two bends, according to an embodiment.

FIG. 1 illustrates a phacoemulsification balanced tip 100 with a proximal end 114 and a cutting edge portion 112 that is bent relative to a tip shaft 108. The balanced tip 100 may include a predominantly straight shaft 108 and at least two bends (first bend 102 and second bend 104) in the cutting edge portion 112. Other numbers of bends are also contemplated (e.g., 3 bends, 4 bends, 7 bends, etc). The balanced tip 100 may be used in conjunction with a phacoemulsification handpiece 204 (e.g., see FIG. 2). When used with the handpiece 204, the balanced tip 100 may be vibrated longitudinally and/or torsionally, i.e., by rotating the tip 100 back and forth around its axis. The bends 102/104 may be positioned, for example, along approximately the distal 5 to 25% of the length of the balanced tip 100) (which may be a portion positioned approximately 5 mm from the distal end point 106 of the tip (measured along the tip axis 116) through to approximately 12 mm from the distal end point 106 of the tip 100). Other portions of the length are also contemplated.

In some embodiments, balancing the tip 100 may include configuring a geometry of the tip 100 (e.g., the geometry of a conical portion 110 of the tip, the shaft 108, and/or the at least first bend 102 and second bend 104) such that, during ultrasonic torsional vibration of the tip 100, a lateral displacement of the shaft 108, perpendicular to the shaft 108, along its length may be less than approximately 5% to 25% (e.g., 15%) of the lateral displacement of the distal end point 106 of the tip 100 (e.g., as measured during frequencies the tip is vibrated at during an ophthalmic procedure). Other thresholds may also be used (e.g., 10 to 20%, 15 to 30%, 10 to 40%, etc). In some embodiments, lateral displacement of the tip (during expected operational frequencies) at the distal end point 106 may be approximately in a range of 30 to 200 microns. As an example, if the distal end point 106 has a lateral displacement of approximately +/− 0.035 mm during ultrasonic torsional vibration of the tip 100, the geometry of the tip may be configured such that the maximum lateral displacement along the shaft is less than 5 microns (other displacements are also possible). As another example, if the distal end point 106 has a lateral displacement of approximately +/− 0.055 mm during ultrasonic torsional vibration of the tip 100, the geometry of the tip may be configured such that the maximum lateral displacement along the shaft is less than 8 microns. In some embodiments, the shaft may extend from the end of a conical portion 110 (which may be, for example, approximately 12 mm from the distal end point 106) through to the first bend 102 in the cutting edge portion 112 (which may be, for example, approximately 5 mm from the distal end point 106). Other locations of the first bend 102 are also contemplated (e.g., 3 mm, 8 mm, etc. from the distal end point 106).

Figure 2:
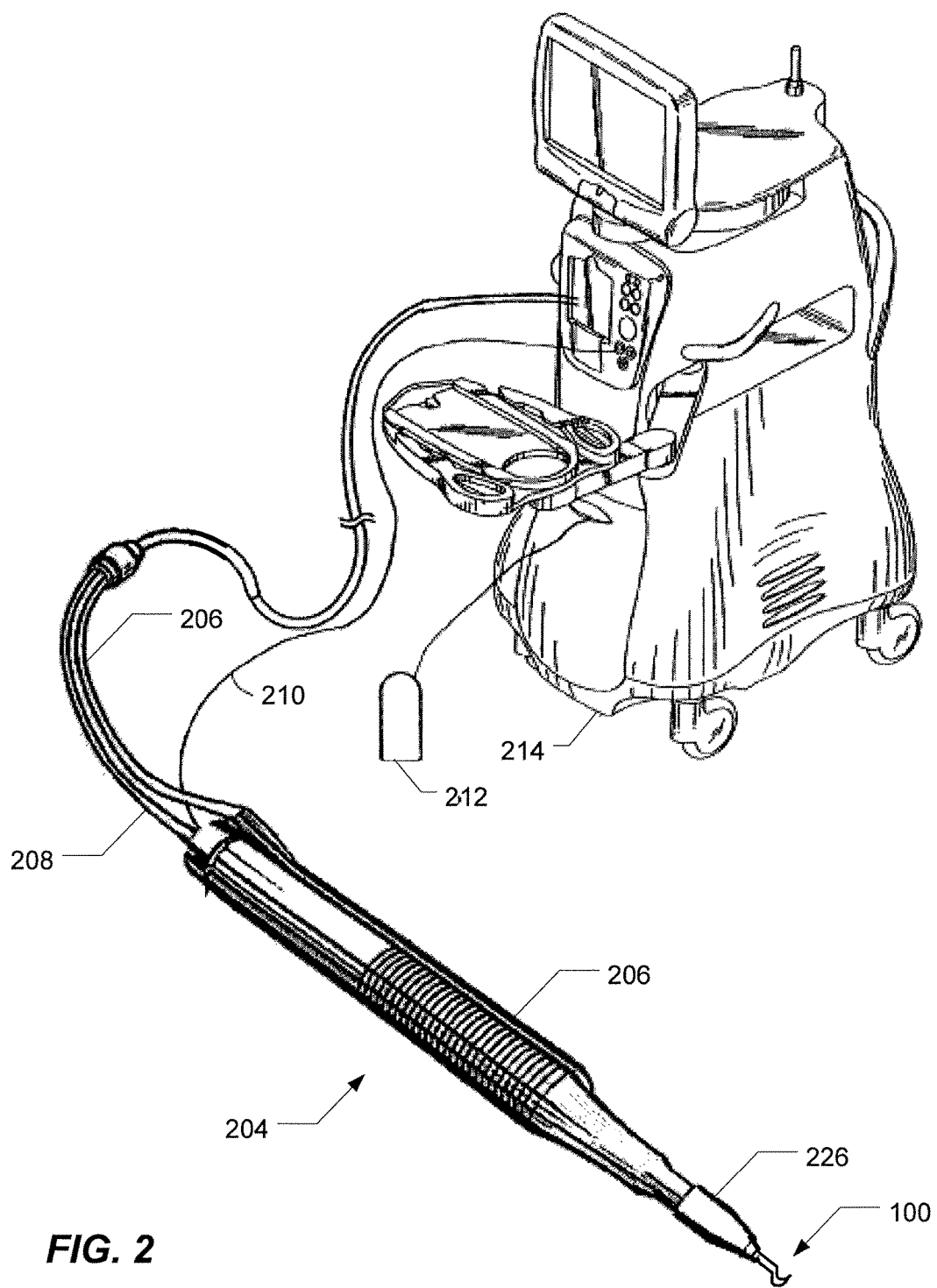
FIG. 2 illustrates a phacoemulsification surgical console connected to a handpiece through an irrigation line and an aspiration line, according to an embodiment.

FIG. 2 illustrates a phacoemulsification surgical console 214 connected to a handpiece 204 through an irrigation line 206 and an aspiration line 208. In some embodiments, power may be supplied to handpiece 204 through electrical cable 210 and flow through irrigation/aspiration lines 206 and 208 may be controlled by a user (e.g., via footswitch 212) to perform a phacoemulsification procedure. One example of a handpiece for a phacoemulsification procedure is described in U.S. Patent Application Publication entitled "Ultrasound Handpiece," Publication No. 2006/0041220, Ser. No. 11/183,591, by Mikhail Boukhny, James Y. Chon, and Ahmad Salehi filed Jul. 18, 2005, which is hereby incorporated by reference in its entirety as though fully and completely set forth herein.

Figure 3:
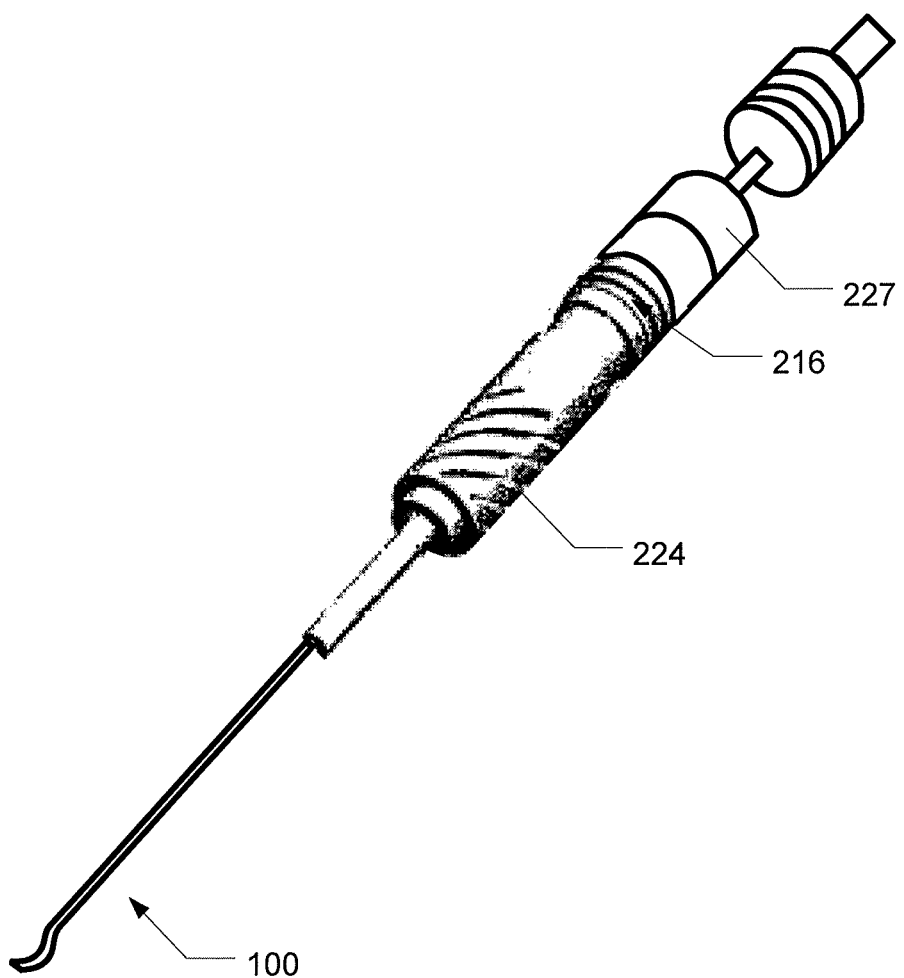
FIG. 3 illustrates an ultrasonic horn attached to the balanced tip, according to an embodiment.

In some embodiments, handpiece 204 may be coupled to a phacoemulsification balanced tip 100. In some embodiments, the handpiece 204 may include at least one set of piezoelectric elements 227 polarized to produce longitudinal motion when excited at a relevant resonant frequency. As seen in FIG. 3, the piezoelectric crystals 227 may be connected to an ultrasonic horn 216 to which a balanced tip 100 is attached. The horn 216 and/or the balanced tip 100 may include a plurality of diagonal slits or grooves 224. The slits or grooves 224 may produce torsional movement in the balanced tip 100 when the piezoelectric crystals are excited at a resonant frequency. Movement of the balanced tip 100 caused by the grooves 224 engaging fixed elements in the handpiece 204 may include a torsional rotational component relative to a centerline of the horn 216.

Figure 4:
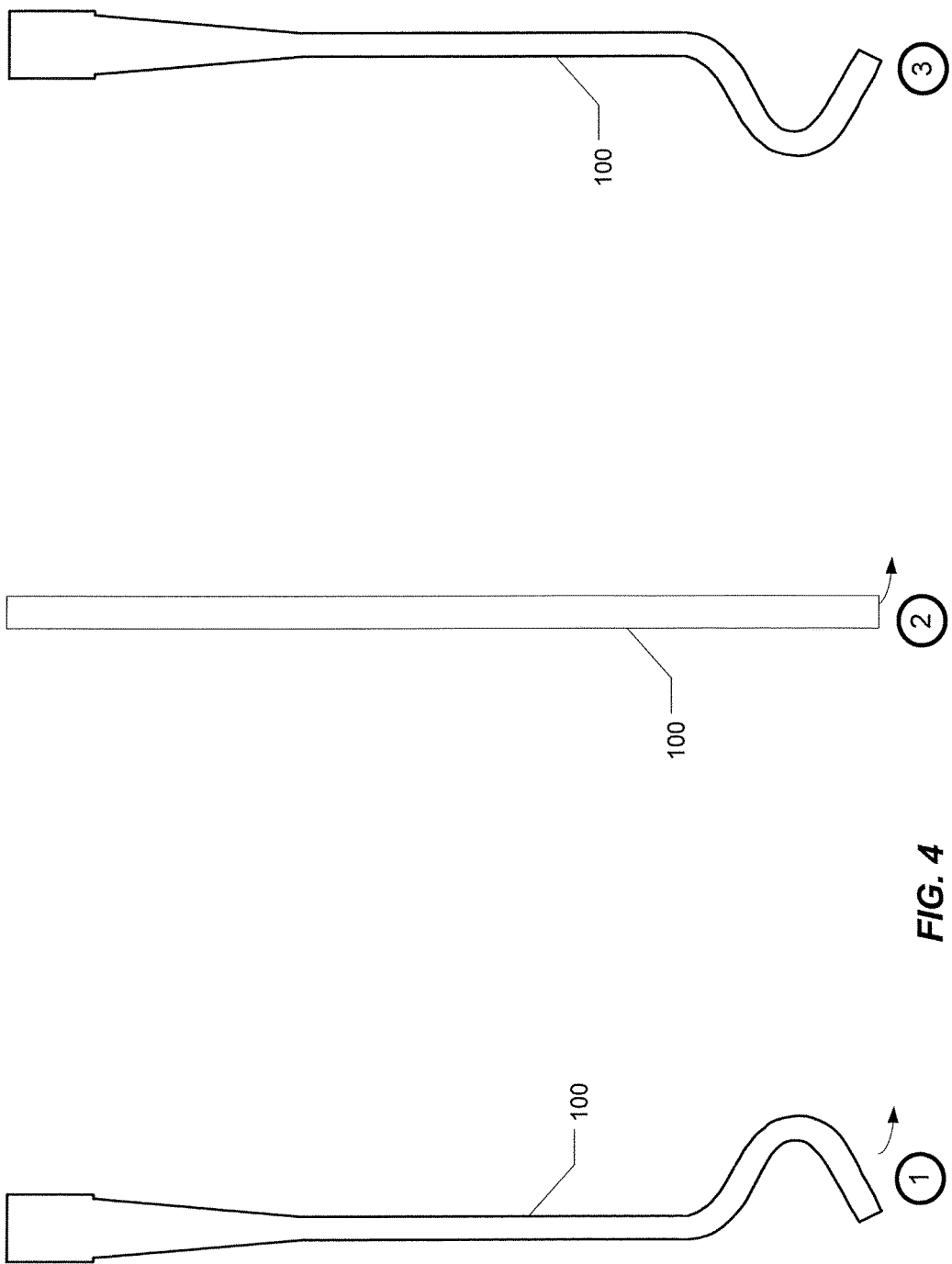
FIG. 4 illustrates motion of the balanced tip, according to an embodiment.

As seen in FIG. 4, in some embodiments, the balanced tip 100 may be configured for ultrasonic torsional rotation back and forth through approximately an arc in the range of approximately 2 to 6 degrees (e.g., an arc of 4 degrees). Other arcs are also contemplated (e.g., 10 degree arc (e.g., plus or minus 5 degrees off center (see middle diagram 2), plus or minus 20 degrees off center, plus or minus 90 degrees off center, etc)). In some embodiments, the balanced tip 100 may be ultrasonically torsionally vibrated at a frequency of approximately between 10-60 kHz (e.g., 31 kHz). Other arcs and frequencies are also contemplated. For example, an arc of plus or minus 20 degrees and/or a frequency of 42 kHz may be used. The arc shown in FIG. 4 is exaggerated to show movement (i.e., the total arc shown is 180 degrees, whereas the balanced tip 100 may have an arc of 4 degrees). In some embodiments, the tip movement in FIG. 4 may also include a longitudinal component (e.g., up and down along an axis parallel to the shaft).

Figure 5:
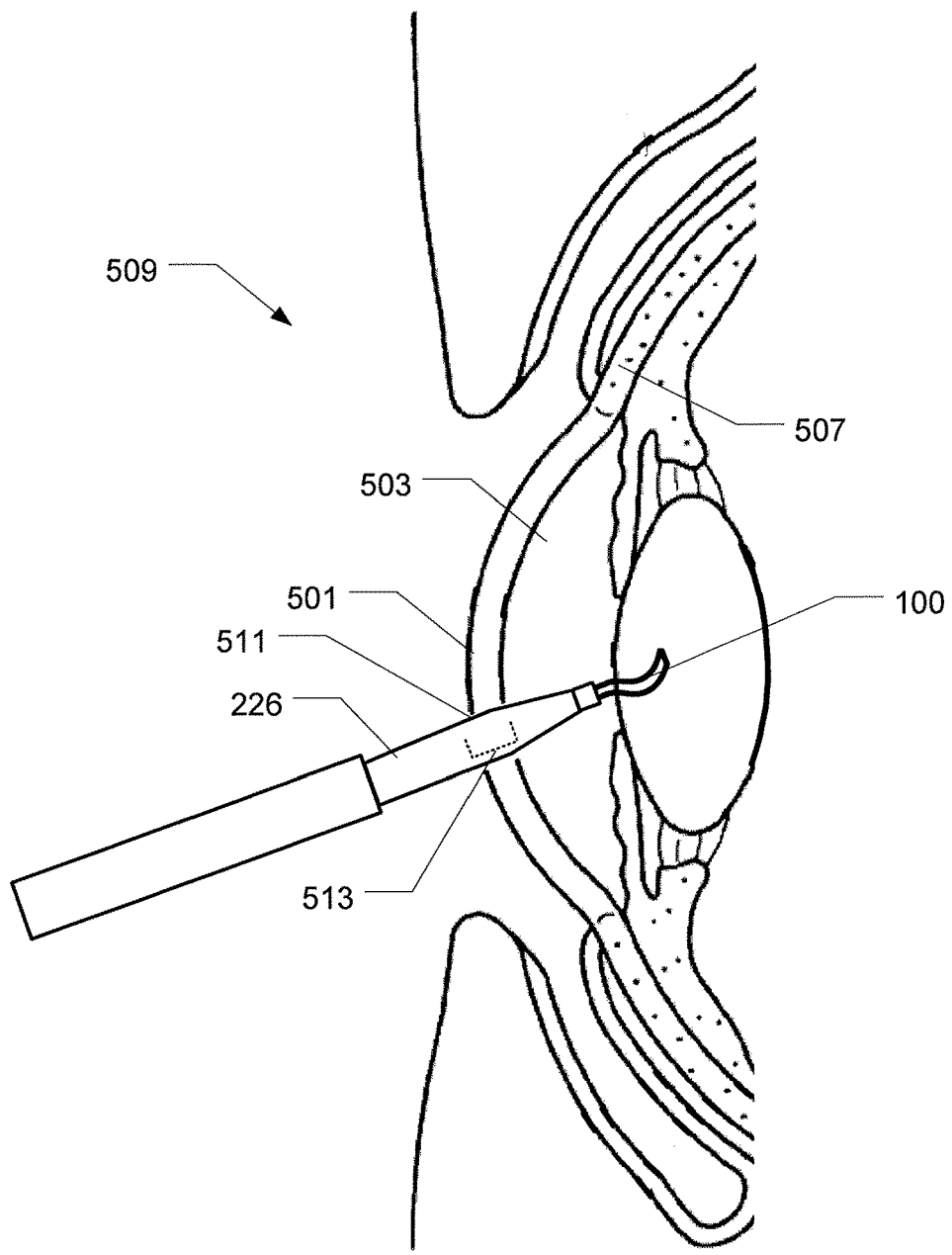
FIG. 5 illustrates a balanced tip inserted into an incision in the eye, according to an embodiment.

As seen in FIG. 5, when used to perform phacoemulsification, the ends of the balanced tip 100 and an irrigating sleeve 226 may be inserted into a small incision 511 in the cornea 501, sclera 507, or other location in the eye tissue to gain access to, for example, the anterior chamber 503 of the eye 509. In various embodiments, a portion or all of the balanced tip 100 may be inside the irrigating sleeve 226. A portion 513 of the tip 100 along the incision 511 may be in thermal contact with the incision 511 (and/or other parts of the eye) through the irrigating sleeve 226 during the phacoemulsification procedure. In some embodiments, the portion 513 along the incision 511 may be in direct contact with the incision 511 (e.g., in the absence of the sleeve 226). The balanced tip 100 may be ultrasonically torsionally vibrated along its longitudinal axis within the irrigating sleeve 226 by a crystal-driven ultrasonic horn 216, thereby emulsifying upon contact the selected tissue in situ. The hollow bore of the balanced tip 100 may communicate with the bore in the horn that in turn may communicate with the aspiration line from the handpiece 204 to the console 214 (e.g., see FIG. 2). A reduced pressure or vacuum source in the console 214 may draw or aspirate the emulsified tissue from the eye 509 through an open end of the balanced tip 100, the bore of the balanced tip 100, the horn bore, and the aspiration line 208 and into a collection device. The aspiration of emulsified tissue may be aided by a saline flushing solution or irrigant that may be injected into the surgical site through the small annular gap between the inside surface of the irrigating sleeve 226 and an outside surface of the balanced tip 100.

Figure 6:
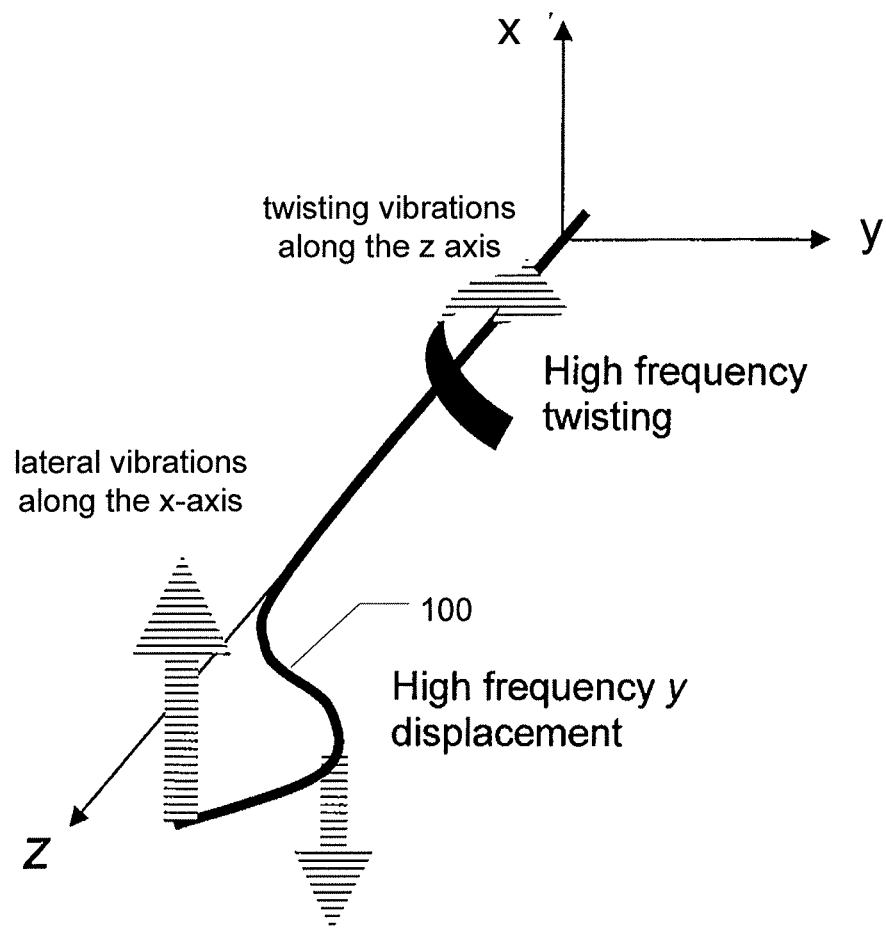
FIG. 6 illustrates twisting vibrations and lateral vibrations relative to the balanced tip, according to an embodiment.

As seen in FIG. 6, ultrasonic torsional vibrations of the balanced tip 100 may result in at least two motions: 1) lateral displacement, of the balanced tip 100 from its equilibrium position, perpendicular to an axis 116 that is collinear with a straight shaft portion (axis 116 may be denoted as the "z-axis") and perpendicular to an axis of a bend of the tip (denoted as y-axis in FIG. 1) (the y-axis and z-axis forming a plane that includes the bend); 2) twist angle along the z axis of the balanced tip 100. An unbalanced tip may have significant bending along the tip length (especially in the shaft) under the action of torsional vibration. By balancing the tip as described herein, lateral displacement along the shaft of the tip 100 may be reduced while the lateral displacement at the distal end point 106 of the tip 100 may be increased. Twisting vibrations may be present in the tip 100 (e.g., twisting back and forth along a twist angle relative to the z axis) which may lead to a relatively large lateral displacement of the distal end point 106 in addition to or in the absence of the lateral displacement of the shaft 108.

In some embodiments, balancing the tip 100 may include adjusting the tip geometry and physically testing a tip with the adjusted tip geometry or using modeling equations or Finite Element Analysis (FEA) to model tip vibrations to find a tip geometry that results in reduced lateral displacement along the shaft 108 with increased lateral displacement and twisting at the distal end point 106 (e.g., using software such as ANSYS). Tip geometry characteristics may include, for example, number of bends (e.g., bends 102, 104), location of the bends, length of the shaft, diameter of the shaft 108, length of the conical portion 110, and diameter of the conical portion. Other tip geometry characteristics may also be modified. In some embodiments, different tip geometries may be tested, for example, by physically creating tips with various tip geometries, vibrating the tips (e.g., using frequencies and modes that are used during phacoemulsification) and monitoring lateral displacement and/or heat generated by the various tip geometries. One or more iterations of testing different tip geometries (e.g., by fixing the location of one bend in the tip and testing different tips with different second bend locations and curvature) may result in identifying one or more optimized tip geometries. Other numbers of bends and geometric modifications (e.g., modifying the location of both bends while holding curvature of both bends constant, modifying the location and curvature of the bends, modifying the number of bends, modifying the length of the shaft, modifying the length of the conical portion, modifying the radius of the shaft, modifying the radii of the conical portion, etc.) are also possible.

Figure 7B:
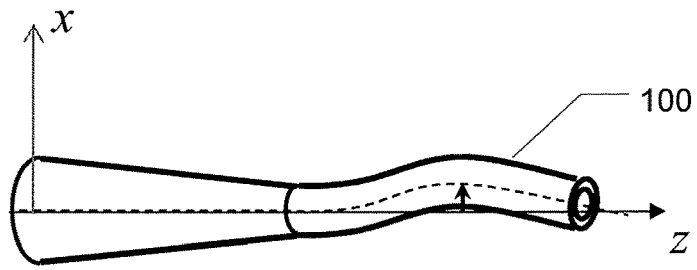
FIG. 7b illustrates model equations for lateral displacement along the z axis of the tip, according to an embodiment.
Figure 7C:
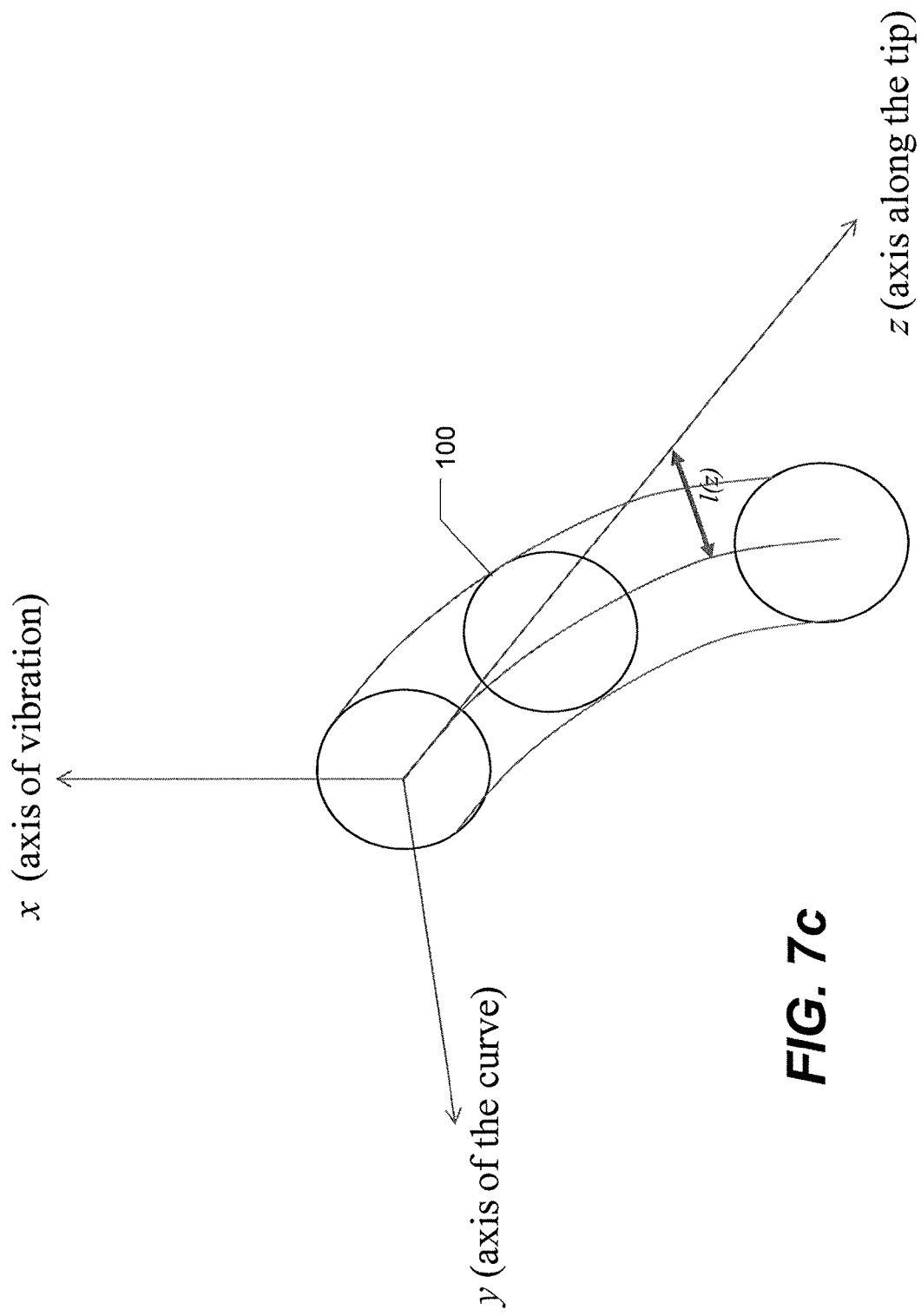
FIG. 7c illustrates a component (l(z)) of the modeling equations, according to an embodiment.

In some embodiments, modeling equations may be used (in place of or in addition to FEA and/or physical testing) to test different tip geometries. For example, the equations describing how the twist angle ($\phi$) and the lateral displacement ($u_x$) vary along the z axis while ultrasonically torsionally vibrating a straight (predominantly cylindrical) tip (e.g., based on the general elasticity theory) may be represented as follows (see also FIGS. 7*a-b*):

$$\ddot{\phi} = \frac{1}{\rho I(z)} \frac{\partial}{\partial z}\left(C(z)\frac{\partial \phi}{\partial z}\right) \text{ where}$$

$$\ddot{\phi} = \frac{\partial^2 \phi}{\partial t^2}; I(z) = \frac{\pi}{2}(R_2^4(z) - R_1^4(z)); C(z) = I(z) * \mu$$

$$\ddot{u}_x = \frac{1}{\rho S(z)} \frac{d^2}{dz^2}\left(EI_y(z)\frac{d^2 u_x}{dz^2}\right) \text{ where}$$

$$\ddot{u}_x = \frac{\partial^2 u_x}{\partial t^2}; I_y(z) = \frac{\pi}{4}(R_2^4(z) - R_1^4(z));$$

$$\text{and } S(z) = \pi(R_2^2(z) - R_1^2(z))$$

Where $\phi$ is the twist angle of the tip, $\rho$ is density of the tip material, $I(z)$ is the moment of inertia of the cylindrical tip cross-section around the z axis, $R_1(z)$ is the inner radius of a hollow inner section of the cylindrical tip body (if the cylindrical body is solid, $R_1(z)$ may be 0 along the entire z axis); $R_2(z)$ is the outer radius of a cylindrical tip body; t is time, $u_x$ is lateral displacement along the x-axis, $S(z)$ is the cross-sectional area of the cylindrical tip along the z axis, E is young's modulus of the tip material, $I_y(z)$ is the moment of inertia of the cross-section of a cylindrical tip around the y axis, and $\mu$ is the torsional modulus of the tip material. Characteristics such as $\rho$ may be the same for the entire tip while characteristics such as $R_1(z)$ and $R_2(z)$ may vary along the z-axis (and thus may be represented, for example, as an array of values). The equations describing how the twist angle ($\phi$) and the lateral displacement ($u_x$) vary along the z axis while ultrasonically torsionally vibrating a curved (predominantly cylindrical) tip (e.g., a tip with bends 102/104) may be represented as follows (see also FIGS. 7*a-b*):

$$\ddot{\phi} = \frac{1}{\rho I(z)} \frac{\partial}{\partial z}\left(C(z)\frac{\partial \phi}{\partial z}\right) - \frac{d^2 l(z)}{dz^2}\left(EI_y(z)\left(\frac{d^2 u_x}{dz^2} - \phi\frac{d^2 l(z)}{dz^2}\right)\right)$$

where $$\ddot{\phi} = \frac{\partial^2 \phi}{\partial t^2}; I(z) = \frac{\pi}{2}(R_2^4(z) - R_1^4(z)); C(z) = I(z) * \mu$$

$$\ddot{u}_x = \frac{1}{\rho S(z)} \frac{d^2}{dz^2}\left(EI_y(z)\left(\frac{d^2 u_x}{dz^2} - \phi\frac{d^2 l(z)}{dz^2}\right)\right) \text{ where}$$

$$\ddot{u}_x = \frac{\partial^2 u_x}{\partial t^2}; I_y(z) = \frac{\pi}{4}(R_2^4(z) - R_1^4(z));$$

$$\text{and } S(z) = \pi(R_2^2(z) - R_1^2(z))$$

Where $\phi$ is the twist angle of the tip, $\rho$ is density of the tip material, $I(z)$ is the moment of inertia of the cylindrical tip cross-section around the z axis, $R_1(z)$ is the inner radius of a hollow inner section of the cylindrical tip body (if the cylindrical body is solid, $R_1(z)$ may be 0); $R_2(z)$ is the outer radius of a cylindrical body; t is time, $u_x$ is lateral displacement along the x-axis, $S(z)$ is the cross-sectional area of the cylindrical tip along the z axis, E is young's modulus of the tip material, $I_y(z)$ is the moment of inertia of the cross-section of a cylindrical tip around the y axis, $\mu$ is the torsional modulus of the tip material, and $l(z)$ is lateral displacement along the y axis as seen in FIG. 7*c*. In some embodiments, one or more of the inputs and/or equations may be modified to account for the presence of a medium the tip is vibrating in (e.g., water, vitreous, etc). For example, the equation for lateral displacement of the tip may be modified as follows:

$$\ddot{u}_x - \gamma \dot{u}_x = \frac{1}{\rho S(z) + \rho_{Media} S_{Media}(z)} \frac{d^2}{dz^2}\left(EI_y(z)\left(\frac{d^2 u_x}{dz^2} - \phi\frac{d^2 l(z)}{dz^2}\right)\right)$$

Where $\gamma$ is an empirical parameter that represents dissipation due to media (such as water). The value of $\gamma$ may be adjusted to align the equation with measured displacements of existing tips in the media. The $\rho_{Media} S_{media}(z)$ term in the denominator represents the increase of the tip mass due to the media that is following the motion of the tip. The $\rho_{Media}$ term is the density of media and the $S_{Media}(z)$ is the cross section of the media moving together with the tip, which may be evaluated using ideal fluid theory as: $S_{Media}(z)=\pi(R_1^2(z)+R_2^2(z))$ (where $R_1$ is the inner diameter of the media mass and $R_2$ is the outer diameter of the media mass following the tip). Other modifications are also contemplated.

In some embodiments, along with the various tip characteristics (e.g., $\rho$, E, etc.), geometric characteristics (e.g., $S(z)$, $I(z)$, $C(z)$, $I_y(z)$, etc.) may be entered by a user or computed by modeling software (e.g., Matlab™) based on other inputs provided by the user (e.g., the user may provide an inner radius (if the tip is hollow in the center), an outer radius of the tip along the z axis, a location (e.g., starting and stopping points (along the z axis) and curvature of one or more bends, etc). The user may also draw the tip shape using a graphical user interface (e.g., see input plots in FIGS. 8*a-b*), the user may preload a tip geometry (e.g., a three dimensional rendering), etc. In some embodiments, the outer radius may be large at values of small z (i.e., in the conical portion of the tip) and relatively small at the end of the tip. Other inputs are also contemplated.

In some embodiments, the solutions for $\phi$ and $u_x$ from the equations above may be used to examine the lateral displacement and twist angles along the z axis for different tip geometries and a balanced/tuned tip geometry may be selected from several tip geometries that maximizes the lateral displacement $u_x$ and twist angle $\phi$ of the distal end point 106 while minimizing the lateral displacement $u_x$ along the tip length (e.g., along the shaft 108). In some embodiments, solving for $\phi$ and $u_x$ may include using harmonic analysis. A solution of the equations for $\phi$ and $u_x$ may provide the twist angle and/or lateral displacements as functions of both z and t (e.g., u(z,t) and $\phi$(z,t)). These solutions may then be used to model the tip according to a harmonic force. Modeling according to a harmonic force may include modeling the tip as if the tip oscillates at some frequency $\omega$ like cos($\omega$t). Harmonics may thus be used to simplify the modeling equations for u(z,t) and $\phi$(z,t) according to the equations for $\ddot{\phi}$ and $\ddot{u}_x$ provided above. In some embodiments, the solution may be modeled according to u(z) cos($\omega$t) (i.e. the vibrational amplitude may be modeled to depend only on z). The formula u(z) cos($\omega$t) may be used in the equations of motion ($\ddot{\phi}$ and $\ddot{u}_x$) to provide a differential equation for the amplitude of vibrations u(z) that is independent of time. The solutions for tip displacement amplitude and twist amplitude may then be plotted (e.g., see outputs in FIGS. 8a-b). In some embodiments, harmonic analysis may not be used (e.g., various solutions dependent on time and z may be determined and analyzed).

Figure 8A:
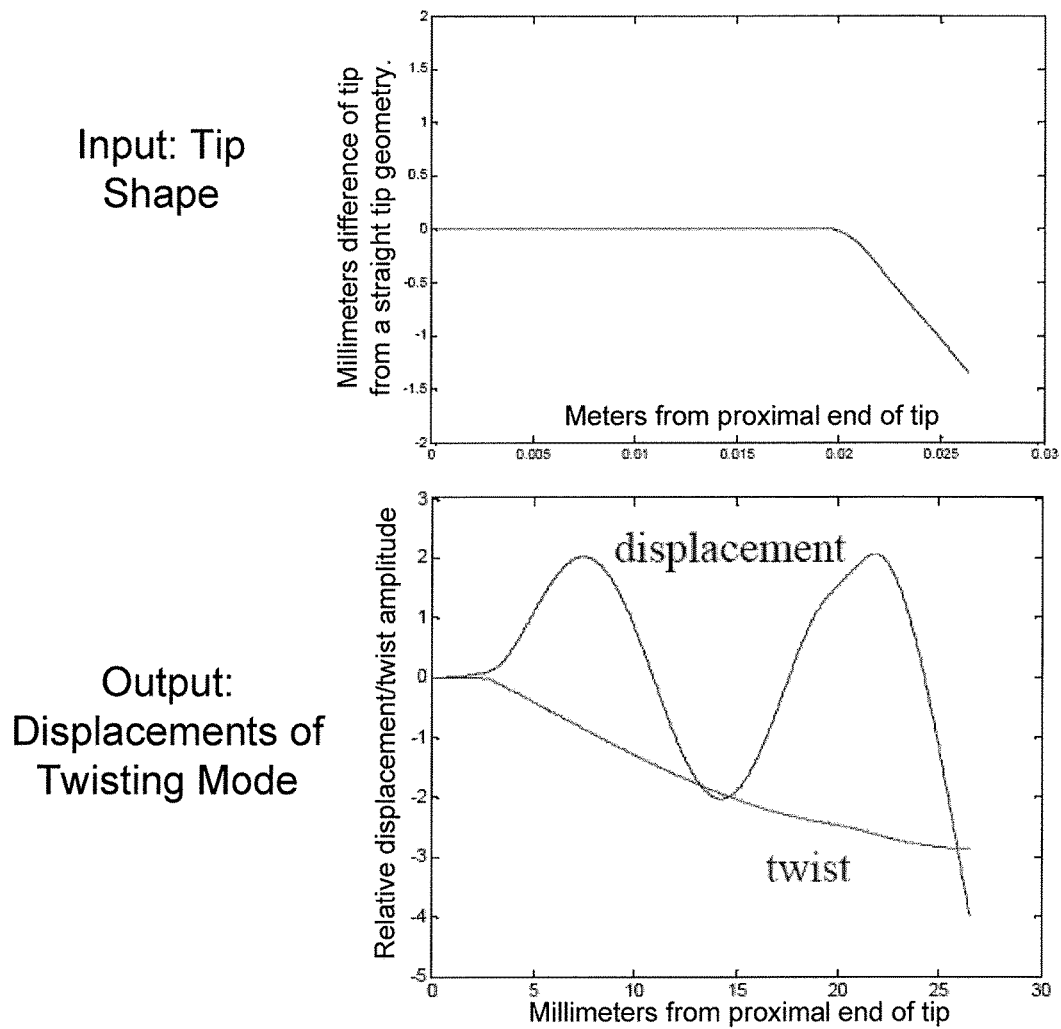
FIGS. 8a-b illustrate embodiments of input tip shapes and corresponding output lateral displacement and twist angle along the tip length according to the model equations.
Figure 8B:
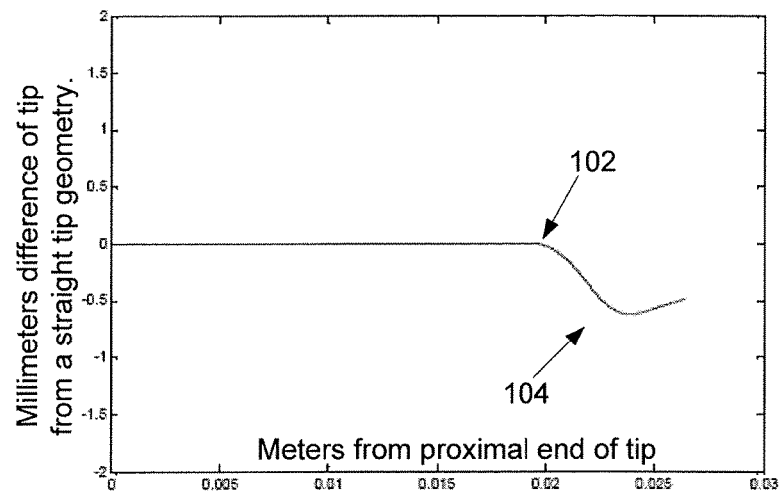
Figure 8B:
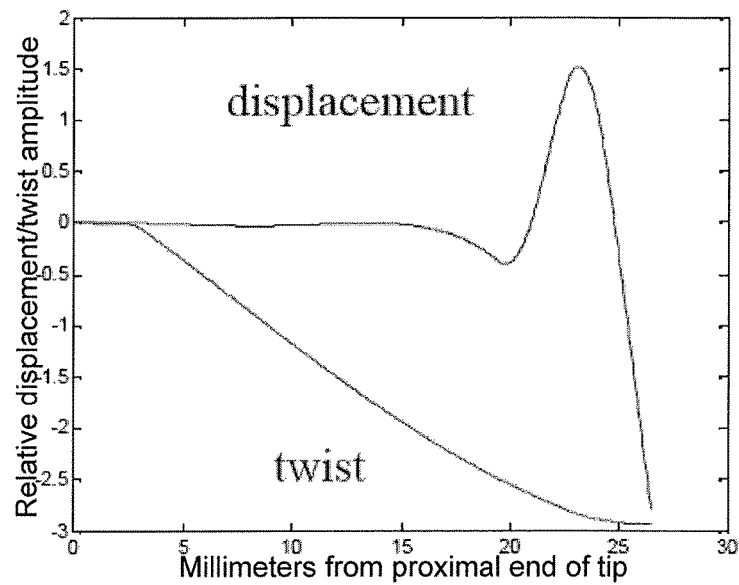

FIGS. 8a-b illustrate input tip shapes and the corresponding displacement and twist angles along the tip length according to the model equations provided above. In some embodiments, the position and the curvature of the first bend 102 may be selected based on various factors such as ergonomics and manufacturing considerations. The second bend 104 may be positioned closer to the distal end point 106 of the balanced tip 100. The curvature of this bend may then be chosen using the prediction of the model equations provided above. The resulting tip shape may then be verified and/or adjusted by performing finite element analysis simulations. The ideal curvature may be such that the twisting vibrational mode and the bending vibrational mode of the balanced tip 100 are uncoupled. The motion of the balanced tip 100 under the torsional force may be the same as its twisting vibrational mode. In some embodiments, the tip bends (e.g., 102/ 104) may be positioned such that the ultrasonic torsional vibration energy in the balanced tip 100 may be in a twisting vibrational mode along a substantial portion of the shaft 108 (with reduced lateral motion). In some embodiments, the length of the shaft 108 may also be adjusted to tune the twisting vibrational mode such that that twisting vibration is in resonance with the ultrasonic driving mechanism (e.g., the piezoelectric elements 227 in the handpiece combined with a horn) to increase twisting displacement at the distal end point 106.

In some embodiments, the amplitude of the distal end point lateral displacement of the balanced tip 100 may depend on the resonance between the torsional driving force and the twisting vibrational mode. While the driving frequency may be set by the torsional horn design, the frequency of the twisting mode may be adjusted by selecting, for example, a length of the conical part 110 of the balanced tip 100. The length of the conical part 110 may be chosen to maximize the twisting vibrations of the balanced tip 100 thus resulting in the maximum twisting displacement of the distal end point 106. Other tip characteristics may also be varied.

In some embodiments, the balanced tip 100 may have a diameter in a range of approximately 0.5 mm to 2 mm (e.g., 1.5 mm). In some embodiments, the balanced tip 100 may have a diameter at a top of the tip of approximately 1.5 mm and a diameter near a distal end of the tip of 0.9 mm (other diameters and configurations are also contemplated). In one embodiment, the balanced tip 100 may have a length of approximately 1 and ⅜ inches and the bends 102, 104 may be located along the distal approximate ⅛ and ⅔ inches. Other dimensions are also contemplated. In some embodiments the first bend 102 may be approximately in a range of −10 to −30 degrees while the second bend 104 may be approximately in a range of 20 to 50 degrees. Other bend angles are also contemplated. The cutting edge portion 112 may have a flared, tapered and/or beveled end (in some embodiments, the cutting edge portion 112 may be flat). Balanced tip 100 may be made from stainless steel or titanium (other materials may also be used). Balanced tip 100 may have an overall length of between 0.50 inches and 1.50 inches (e.g., 1.20 inches). Other lengths are also contemplated. Balanced tip 100 may be formed using conventional metalworking technology and may be electropolished. Shaft 108 may be generally tubular, with an outside diameter of between 0.005 inches and 0.100 inches and an inside diameter of between 0.001 inches and 0.090 inches (other diameters are also contemplated).

Figure 9:
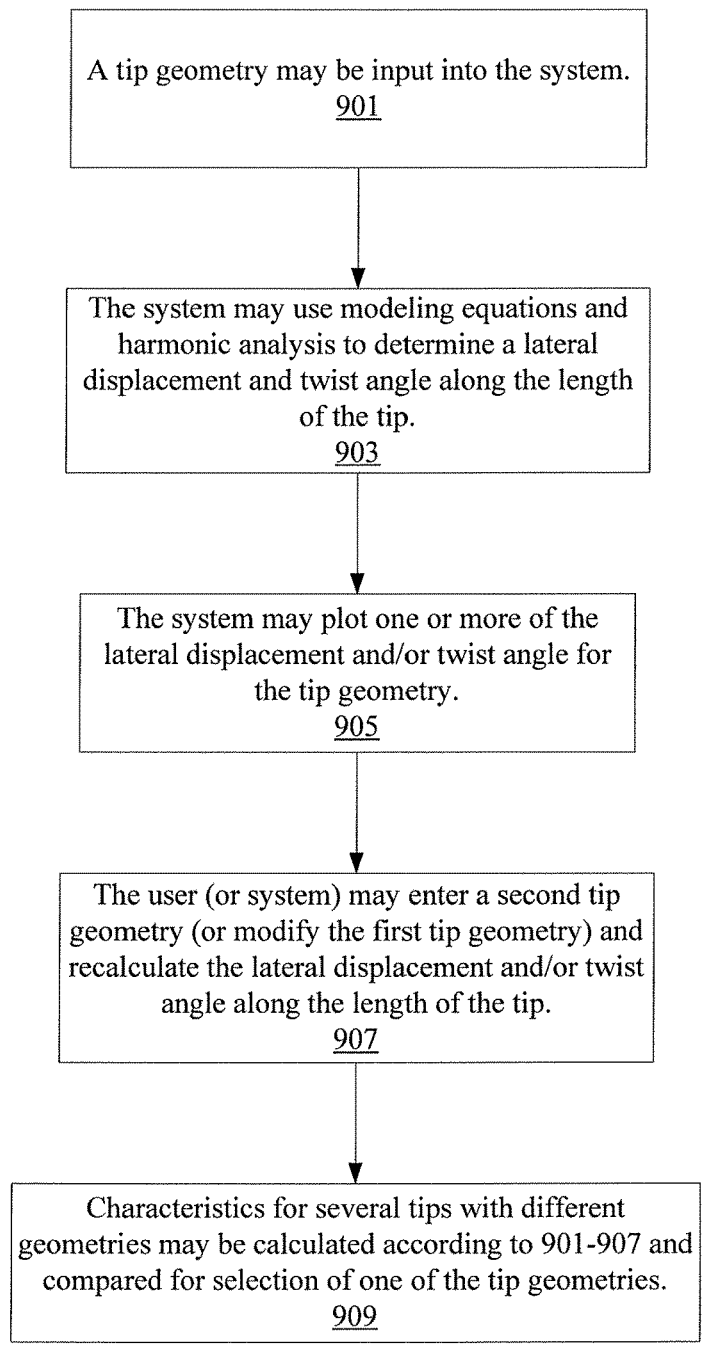
FIG. 9 illustrates a flowchart of the method for determining a tip geometry, according to an embodiment.

FIG. 9 illustrates a flowchart of the method for determining a tip geometry, according to an embodiment. The elements provided in the flowchart are illustrative only. Various provided elements may be omitted, additional elements may be added, and/or various elements may be performed in a different order than provided below.

At 901, a tip geometry may be input into the system. For example, geometry inputs may be stored in an input file. In some embodiments, the tip geometry may include one or more of the following defined as values of the geometry at slices of the tip (e.g., the tip may be divided into 500 slices and the geometric characteristics of the tip at each slice may be stored in a separate array assigned to a respective geometric variable). For example, geometric characteristics for the tip slices may include curvature (e.g., in degrees), torsional rigidity (e.g., C(z)), moment of inertia around the x-axis (e.g., I(z)), cross sectional area (e.g., S(z)), moment of inertia of the slice around the y-axis that controls the bending rigidity of the tip (e.g., $I_y(z)$), distance of the tip from the z-axis (e.g., l(z)). Other inputs are also contemplated.

In some embodiments, these slice based arrays may be input directly by a user or may be calculated based on other geometric inputs. For example, the user may provide a length of the tip, the length of the conical portion, the location along the tip where the first bend starts, the location along the tip where the first bend ends, the curvature of the first bend, the location along the tip where the second bend starts, the location along the tip where the second bend ends, the curvature of the second bend, the shear modulus of the tip material, young's modulus for the tip material, the density of the tip material, etc. and the specific inputs for the different slices may be calculated and stored in an input file or provided to modeling software. In some embodiments, the computer system may generate the inputs automatically. For example, the computer system may cycle through various iterations of possible tip geometries. In some embodiments, the user may draw a tip (e.g., through a graphical user interface) and the computer system may calculate the geometry based on the drawing. Other input types are also contemplated.

At 903, the system may use modeling equations and harmonic analysis to determine a lateral displacement and twist angle along the length of the tip for the given tip geometry and ultrasonic torsional vibration frequency (e.g., approximately 31 kHz). Other frequencies are also contemplated. For example, the equations $$\ddot{u}_x = \frac{1}{\rho S(z)} \frac{d^2}{dz^2}\left(EI_y(z)\left(\frac{d^2 u_x}{dz^2} - \phi \frac{d^2 l(z)}{dz^2}\right)\right) \text{ and}$$

$$\ddot{\phi} = \frac{1}{\rho I(z)} \frac{\partial}{\partial z}\left(C(z)\frac{\partial \phi}{\partial z}\right) - \frac{d^2 l(z)}{dz^2}\left(EI_y(z)\left(\frac{d^2 u_x}{dz^2} - \phi \frac{d^2 l(z)}{dz^2}\right)\right)$$

may be solved for $u_x$ and $\phi$ using inputs (as defined above) and harmonic analysis (e.g., using harmonics with $u(z)$ $\cos(\omega t)$, $\phi(z) \cos(\omega t)$) to simplify the results by removing time. According to harmonic analysis, in some embodiments, it may be assumed that:

$$u_x(z,t)=u(z)\cos(\omega t), \text{and } \phi(z,t)=\varphi(z)\cos(\omega t)$$

By taking a time derivative:

$$\cos(\omega t)''=-\omega^2 \cos(\omega t)$$

and substituting it into the original equations and cancelling the time cosine one may obtain time independent equations:

$$-\omega^2 u(z) = \frac{1}{\rho S(z)} \frac{d^2}{dz^2}\left(EI_y(z)\left(\frac{d^2 u(z)}{dz^2} - \varphi(z)\frac{d^2 l(z)}{dz^2}\right)\right) \text{ and}$$

$$-\omega^2 \varphi(z) = \frac{1}{\rho I(z)} \frac{\partial}{\partial z}\left(C(z)\frac{\partial \varphi(z)}{\partial z}\right) - \frac{d^2 l(z)}{dz^2}\left(EI_y(z)\left(\frac{d^2 u(z)}{dz^2} - \varphi(z)\frac{d^2 l(z)}{dz^2}\right)\right)$$

The above equations may then solved for the amplitudes of displacement $u(z)$ and the twist angle $\varphi(z)$. Other equations for solving $u_x$ may also be used.

At 905, the system may plot one or more of the lateral displacement and/or twist angle for the tip geometry (e.g., see FIG. 8a-8b).

At 907, the user (or system) may provide a second tip geometry (or modify the first tip geometry) and recalculate the lateral displacement ($u_x$) and twist angle ($\phi$) along the length of the tip. Other modeling techniques may also be used. For example, finite element analysis (FEA) may be used to determine lateral displacement ($u_x$) and/or twist angle ($\phi$) along the length of tips of various geometries subjected to various vibrations. Further, other equations may also be used (e.g., different equations may be used for square tip modeling).

At 909, characteristics for several tips with different geometries may be calculated according to 901-907 and compared for selection of one of the tip geometries (or generation of a new tip geometry to analyze). Selecting one of the tip geometries may include selecting a tip geometry based on which tip geometry has a smaller lateral displacement along a portion of the tip shaft configured to be along an incision in an eye during a phacoemulsification procedure. In some embodiments, if the lateral displacement (of the analyzed tip geometries) along a portion of the tip shaft configured to be along an incision in an eye during a phacoemulsification procedure (e.g., throughout a portion of the shaft that extends from the proximal end of the shaft (such as the end of the conical portion) to the first bend of the cutting edge portion) is greater than approximately 5% to 25% (e.g., 15%) of the lateral displacement of the distal end point 106, (other thresholds (e.g., 1 micron, 2 microns, 100 microns, 2 mm, etc.) may also be used), another tip geometry may be generated, the lateral displacement of the new tip geometry may be modeled and compared to at least one of the lateral displacement of the first or second tip geometry for further selection between the first, second, and new geometry (at which point, one of the tips may be selected or another tip geometry may be generated for comparison purposes).

In some embodiments, generating new geometries may include modifying the previously tested geometries for additional modeling. In some embodiments, the user may further modify a selected tip geometry to tune the geometry according to additional criteria. For example, the user may modify the length of the conical part 110 (or other geometric characteristics such as length of the shaft) to increase the twisting vibrations of the balanced tip 100 to provide a greater lateral displacement of the distal end point 106. In some embodiments, the user may try different locations and curvatures of one or more of the bends to reduce the lateral displacement toward the proximal end of the tip while increasing the lateral displacement toward the distal end of the tip. The modifications may be used for a third, fourth, etc. tip and the results compared to previous tip results to optimize the selection of the geometric characteristics of the tip.

Figure 10:
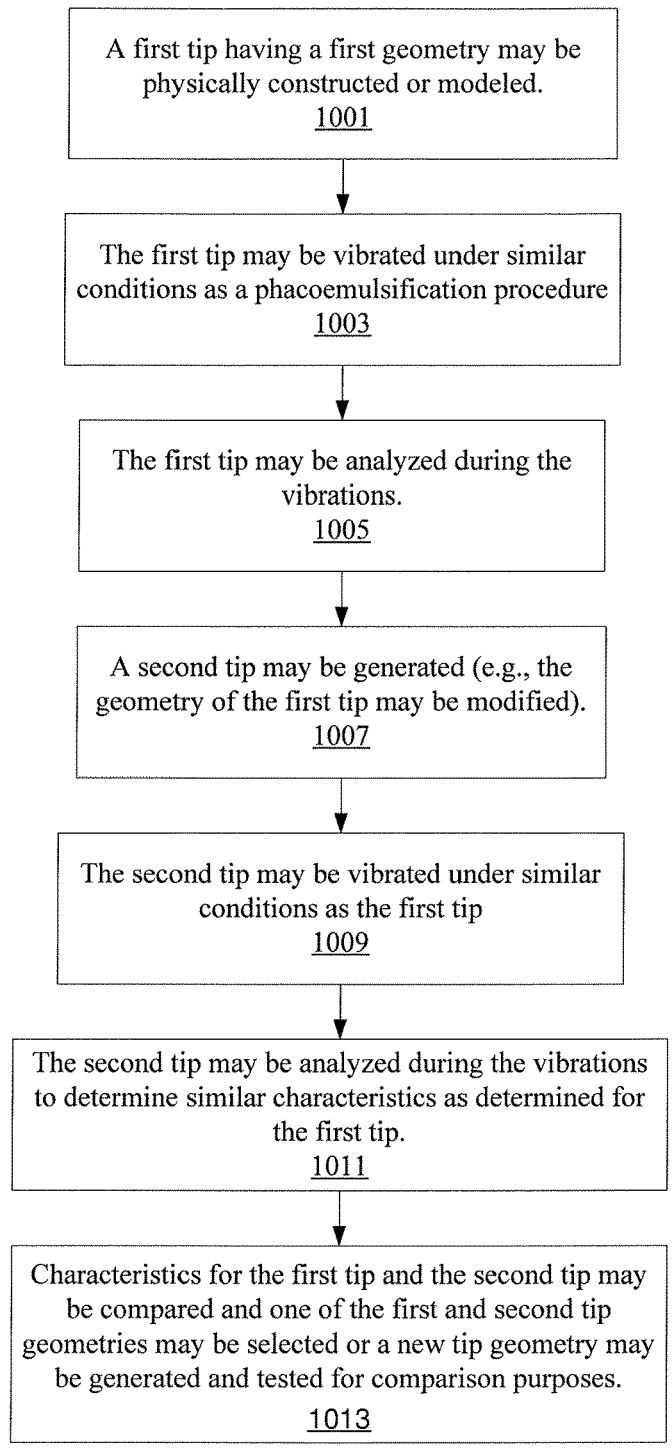
FIG. 10 illustrates a flowchart of another method for determining a tip geometry, according to an embodiment.

FIG. 10 illustrates a flowchart of another method for determining a tip geometry, according to an embodiment. The elements provided in the flowchart are illustrative only. Various provided elements may be omitted, additional elements may be added, and/or various elements may be performed in a different order than provided below.

At 1001, a first tip having a first geometry may be physically constructed or modeled (e.g., using Finite Element Analysis). In some embodiments, the first tip may have a circular cross section, square cross section, or a cross section that varies along an axis of the tip.

At 1003, the first tip may be vibrated under similar conditions as a phacoemulsification procedure (e.g., by being secured in a phacoemulsification handpiece as shown in FIGS. 2-3 and vibrated at a frequency of approximately 31 kHz and/or being "vibrated" using modeling software such as ANSYS). Other frequencies are also contemplated (e.g., approximately between 10 kHz and 60 kHz). In some embodiments, the first tip may be secured to a phacoemulsification handpiece to be vibrated. In some embodiments, the tip may be secured to a different apparatus (e.g., a test fixture) for applying the vibrations. In some embodiments, the end of the first tip may be placed in water or a material with similar characteristics as vitreous (other liquids are also contemplated). In some embodiments, the first tip may include two bends (e.g., 102, 104). Other numbers of bends are also contemplated.

At 1005, the first tip may be analyzed during the vibrations. For example, thermal imaging, stroboscopy, physical measurement of displacement, etc. may be used to determine lateral displacement ($u_x$) and/or twist angle ($\phi$) (or characteristics indicative of lateral displacement ($u_x$) and/or twist angle ($\phi$)) for the tip. For example, in a thermal scan of the vibrating tip, locations of higher heat along the tip length may be indicative of larger lateral displacements ($u_x$).

At 1007, a second tip may be constructed (e.g., the geometry of the first tip may be modified). Modifications may be made to different geometric characteristics as provided above. For example, the location and/or curvature of the second bend 104 may be modified.

At 1009, the second tip may be vibrated under similar conditions as the first tip.

At 1011, the second tip may be analyzed during the vibrations to determine similar characteristics (such as lateral displacement and twist angle) as determined for the first tip.

At 1013, characteristics for the first tip and the second tip may be compared and one of the first and second tip geometries may be selected or a new tip geometry may be generated and tested for comparison purposes. For example, selecting the first tip geometry or the second tip geometry may be based on which tip geometry has a smaller lateral displacement along a portion of the tip shaft configured to be along an incision in an eye during a phacoemulsification procedure. In some embodiments, if the lateral displacement along a portion of the tip shaft configured to be along an incision in an eye during a phacoemulsification procedure (e.g., throughout a portion of the shaft that extends from the proximal end of the shaft (such as the end of the conical portion) to the first bend of the cutting edge portion) is greater than approximately 5% to 25% (e.g., 15%) (as noted above, other thresholds are also possible) of the displacement of the distal end point 106 of the tip, a third tip may be generated and tested. The lateral displacement and/or twist angle of the third tip geometry may be determined and compared to the lateral displacement and/or twist angle of the first or second tip geometry for further selection between the first, second, and third tip geometries (at which point, one of the tips may be selected or another tip geometry may be generated for comparison purposes).

FIG. 11 illustrates six possible balanced tip embodiments (other embodiments are also possible). The balanced tip 100 may have a geometry according to one of the sets of parameters provided in the FIG. 11 table. The balanced tip 100 may have an outside diameter of OD inches; a diameter of the inside bore of ID inches; a total length of L inches from the hub (the proximal point of the tip 100 that is configured to attach to the ultrasonic horn) to the distal end point 106 of the tip 100. The conical portion 110 of the tip 100 may extend $L_c$ inches from the hub. The first bend 102 of the tip 100 may have an angle of $\alpha_1$ degrees and extend between points lying at a distance of $x_1$ and $x_2$ inches from the distal end point 106. The second bend 104 may have the angle of $\alpha_2$ degrees and extend between points lying at a distance of $y_1$ and $y_2$ inches from the distal end point 106. The cutting edge portion 112 may have a beveled edge (i.e., at the distal most edge of the cutting edge portion) that is facing up 30 or 45 degrees or facing down 30 degrees as indicated in the table (as an example, the bevel shown in FIG. 1 is facing down).

In some embodiments, a modeling system may include one or more processors. The processor may include single processing devices or a plurality of processing devices. Such a processing device may be a microprocessor, controller (which may be a micro-controller), digital signal processor, microcomputer, central processing unit, field programmable gate array, programmable logic device, state machine, logic circuitry, control circuitry, analog circuitry, digital circuitry, and/or any device that manipulates signals (analog and/or digital) based on operational instructions. The memory coupled to and/or embedded in the processors may be a single memory device or a plurality of memory devices. Such a memory device may be a read-only memory, random access memory, volatile memory, non-volatile memory, static memory, dynamic memory, flash memory, cache memory, and/or any device that stores digital information. Note that when the processors implement one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. The memory may store, and the processor may execute, operational instructions corresponding to at least some of the elements illustrated and described in association with the figures (e.g., FIGS. 9 and 10).

Various modifications may be made to the presented embodiments by a person of ordinary skill in the art. Other embodiments of the present invention will also be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A balanced phacoemulsification tip, comprising:
    a shaft having a proximal end and a distal end;
    a cutting edge portion at the distal end of the shaft, wherein the cutting edge portion comprises at least a first and second bend;
    wherein a geometry of the shaft and the at least first and second bend is configured to result in a lateral displacement, perpendicular to the shaft, during ultrasonic torsional vibration of the tip, of less than approximately 5 to 25% of a lateral displacement at a distal end point of the tip throughout a portion of the shaft that extends from the proximal end of the shaft to the first bend of the cutting edge portion;
    wherein the at least first and second bends are positioned such that ultrasonic torsional vibration energy in the shaft during ultrasonic torsional vibration is in a twisting vibrational mode along a substantial portion of the shaft.

2. The balanced phacoemulsification tip of claim 1, wherein the lateral displacement ($u_x$) perpendicular to the shaft is at least partially defined using an equation $$\ddot{u}_x = \frac{1}{\rho S(z)} \frac{d^2}{dz^2} \left( EI_y(z) \left( \frac{d^2 u_x}{dz^2} - \phi \frac{d^2 l(z)}{dz^2} \right) \right),$$

wherein:
    $\phi$ is a twist angle of the tip,
    $\rho$ is density of a tip material,
    $S(z)$ is a cross-sectional area of the tip along an axis collinear with the shaft,
    E is young's modulus of the tip material,
    $I_y(z)$ is a moment of inertia of a cross-section of the tip around an axis perpendicular to the axis collinear with the shaft, and
    $l(z)$ is lateral displacement along an axis perpendicular to the axis collinear with the shaft.

3. The balanced phacoemulsification tip of claim 2, wherein $\phi$ is provided through an equation $$\ddot{\phi} = \frac{1}{\rho I(z)} \frac{\partial}{\partial z} \left( C(z) \frac{\partial \phi}{\partial z} \right) - \frac{d^2 l(z)}{dz^2} \left( EI_y(z) \left( \frac{d^2 u_x}{dz^2} - \phi \frac{d^2 l(z)}{dz^2} \right) \right)$$

where $I(z)$ is a moment of inertia of a cylindrical tip cross-section around the axis collinear with the shaft, $C(z) = I(z) * \mu$, and $\mu$ is a torsional modulus of the tip material.

4. The balanced phacoemulsification tip of claim 3, wherein equations $$\ddot{u}_x = \frac{1}{\rho S(z)} \frac{d^2}{dz^2}\left(EI_y(z)\left(\frac{d^2 u_x}{dz^2} - \phi \frac{d^2 l(z)}{dz^2}\right)\right)$$

and $$\ddot{\phi} = \frac{1}{\rho I(z)} \frac{\partial}{\partial z}\left(C(z)\frac{\partial \phi}{\partial z}\right) - \frac{d^2 l(z)}{dz^2}\left(EI_y(z)\left(\frac{d^2 u_x}{dz^2} - \phi \frac{d^2 l(z)}{dz^2}\right)\right)$$

are solved through harmonic analysis.

5. The balanced phacoemulsification tip of claim 1, wherein a proximal end of the tip includes a conical portion and wherein a length of the conical portion is selected to increase twisting vibrations of the tip during ultrasonic torsional vibrations to provide a greater lateral displacement at the distal end point of the tip.

6. The balanced phacoemulsification tip of claim 1, further comprising a hollow bore through the tip in communication with a vacuum source.

7. The balanced phacoemulsification tip of claim 1, wherein the ultrasonic torsional vibration comprises ultrasonic torsional rotation back and forth on an arc approximately in a range of 2 to 6 degrees.

8. The balanced phacoemulsification tip of claim 1, wherein the tip is made of stainless steel or titanium.

9. The balanced phacoemulsification tip of claim 1, wherein the cutting edge portion is flared, tapered, beveled, or flat.

10. The balanced phacoemulsification tip of claim 1, wherein a length of the shaft is selected to tune the twisting vibrational mode such that a twisting vibration is in resonance with an ultrasonic driving mechanism to increase twisting displacement at the distal end point of the tip.

11. The balanced phacoemulsification tip of claim 1, wherein the first bend has an angle of approximately −19 degrees and extends approximately 0.252 to 0.153 inches from the distal end point and the second bend has an angle of approximately 37 degrees and extends approximately 0.152 to 0.055 inches from the distal end point.

12. The balanced phacoemulsification tip of claim 1, wherein the first bend has an angle of approximately −19 degrees and extends approximately 0.258 to 0.155 inches from the distal end point and the second bend has an angle of approximately 36 degrees and extends approximately 0.154 to 0.060 inches from the distal end point.

13. The balanced phacoemulsification tip of claim 1, wherein the first bend has an angle of approximately −19 degrees and extends approximately 0.252 to 0.153 inches from the distal end point and the second bend has an angle of approximately 36 degrees and extends approximately 0.152 to 0.058 inches from the distal end point.

14. The balanced phacoemulsification tip of claim 1, wherein the first bend has an angle of approximately −12 degrees and extends approximately 0.238 to 0.121 inches from the distal end point and the second bend has an angle of approximately 27 degrees and extends approximately 0.121 to 0.043 inches from the distal end point.

15. The balanced phacoemulsification tip of claim 1, wherein the first bend has an angle of approximately −12 degrees and extends approximately 0.244 to 0.127 inches from the distal end point and the second bend has an angle of approximately 27 degrees and extends approximately 0.127 to 0.049 inches from the distal end point.

16. The balanced phacoemulsification tip of claim 1, further comprising:
   piezoelectric elements polarized to produce longitudinal motion when excited at a resonant frequency; and
   a horn coupled to the shaft and the piezoelectric elements, wherein the horn comprises a plurality of grooves to produce the ultrasonic torsional vibration in the balanced phacoemulsification tip at a frequency approximately in a range of 10 kHz to 60 kHz when the piezoelectric elements are excited at the resonant frequency.

17. A balanced phacoemulsification tip, comprising:
   a shaft having a proximal end and a distal end;
   a cutting edge portion at the distal end of the shaft, wherein the cutting edge portion comprises at least a first and second bend;
   wherein a geometry of the shaft and the at least first and second bend is configured to result in a lateral displacement, perpendicular to the shaft, during ultrasonic torsional vibration, at a frequency approximately in a range of 10 kHz to 60 kHz, of the tip, of less than approximately 5 to 25% of a lateral displacement at a distal end point of the tip throughout a portion of the shaft that extends from the proximal end of the shaft to the first bend of the cutting edge portion;
   wherein the at least first and second bends are positioned such that ultrasonic torsional vibration energy in the shaft during ultrasonic torsional vibration is in a twisting vibrational mode along a substantial portion of the shaft;
   wherein a length of the shaft is selected to tune the twisting vibrational mode such that a twisting vibration is in resonance with an ultrasonic driving mechanism to increase twisting displacement at the distal end point of the tip;
   wherein the lateral displacement of the tip at the distal end point of the tip is approximately in a range of 40 to 200 microns;
   wherein the ultrasonic torsional vibration comprises ultrasonic torsional rotation back and forth on an arc approximately in a range of 2 to 6 degrees.

18. The balanced phacoemulsification tip of claim 17, wherein the proximal end of the tip includes a conical portion and wherein a length of the conical portion is selected to increase twisting vibrations of the tip during ultrasonic torsional vibrations to provide a greater lateral displacement at the distal end point of the tip.

19. A balanced phacoemulsification tip, comprising:
   a shaft having a proximal end and a distal end;
   a cutting edge portion at the distal end of the shaft, wherein the cutting edge portion comprises at least a first and second bend;
   wherein a geometry of the shaft and the at least first and second bend is configured to result in a lateral displacement, perpendicular to the shaft, during ultrasonic torsional vibration of the tip, of less than approximately 5 to 25% of a lateral displacement at a distal end point of the tip throughout a portion of the shaft that extends from the proximal end of the shaft to the first bend of the cutting edge portion;
   wherein the at least first and second bends are positioned such that ultrasonic torsional vibration energy in the shaft during ultrasonic torsional vibration is in a twisting vibrational mode along a substantial portion of the shaft;
   wherein a length of the shaft is selected to tune the twisting vibrational mode such that a twisting vibration is in resonance with an ultrasonic driving mechanism to increase twisting displacement at the distal end point of the tip;

wherein the lateral displacement ($u_x$) perpendicular to the shaft is at least partially defined using an equation $$\ddot{u}_x = \frac{1}{\rho S(z)} \frac{d^2}{dz^2}\left(EI_y(z)\left(\frac{d^2 u_x}{dz^2} - \phi \frac{d^2 l(z)}{dz^2}\right)\right),$$

wherein:
$\phi$ is a twist angle of the tip,
$\rho$ is density of a tip material,
$S(z)$ is a cross-sectional area of the tip along an axis collinear with the shaft,
E is young's modulus of the tip material,
$I_y(z)$ is a moment of inertia of a cross-section of the tip around an axis perpendicular to the axis collinear with the shaft, and
$l(z)$ is lateral displacement along an axis perpendicular to the axis collinear with the shaft;
wherein $\phi$ is provided through an equation $$\ddot{\phi} = \frac{1}{\rho I(z)} \frac{\partial}{\partial z}\left(C(z)\frac{\partial \phi}{\partial z}\right) - \frac{d^2 l(z)}{dz^2}\left(EI_y(z)\left(\frac{d^2 u_x}{dz^2} - \phi \frac{d^2 l(z)}{dz^2}\right)\right)$$

where $I(z)$ is a moment of inertia of a cylindrical tip cross-section around the axis collinear with the shaft, $C(z) = I(z)* \mu$, and $\mu$ is a torsional modulus of the tip material;

wherein equations $$\ddot{u}_x = \frac{1}{\rho S(z)} \frac{d^2}{dz^2}\left(EI_y(z)\left(\frac{d^2 u_x}{dz^2} - \phi \frac{d^2 l(z)}{dz^2}\right)\right)$$

and $$\ddot{\phi} = \frac{1}{\rho I(z)} \frac{\partial}{\partial z}\left(C(z)\frac{\partial \phi}{\partial z}\right) - \frac{d^2 l(z)}{dz^2}\left(EI_y(z)\left(\frac{d^2 u_x}{dz^2} - \phi \frac{d^2 l(z)}{dz^2}\right)\right)$$

are solved through harmonic analysis;

further comprising a hollow bore through the tip in communication with a vacuum source;

wherein the ultrasonic torsional vibration comprises a frequency approximately in a range of 10 kHz to 60 kHz; and wherein the ultrasonic torsional vibration comprises ultrasonic torsional rotation back and forth on an arc approximately in a range of 2 to 6 degrees.

20. The balanced phacoemulsification tip of claim 19, wherein the proximal end of the tip includes a conical portion and wherein a length of the conical portion is selected to increase twisting vibrations of the tip during ultrasonic torsional vibrations to provide a greater lateral displacement at the distal end point of the tip.

* * * * *